US005843450A

United States Patent [19]

Dawson et al.

[11] Patent Number: 5,843,450
[45] Date of Patent: Dec. 1, 1998

[54] HEPATITIS GB VIRUS SYNTHETIC PEPTIDES AND USES THEREOF

[75] Inventors: George J. Dawson, Libertyville; Tami J. Pilot-Matias, Green Oaks; Dominique P. Bridon, Morton Grove; Pamella A. Schroeder-Poliak, Hawthorn Woods; Mark F. Knigge, Grayslake, all of Ill.; Keeve D. Jaffe, Trevor, Wis.; Isa K. Mushahwar, Grayslake, Ill.

[73] Assignee: Abbott Laboratories, Abbott Park, Ill.

[21] Appl. No.: 473,475

[22] Filed: Jun. 7, 1995

Related U.S. Application Data

[63] Continuation-in-part of Ser. No. 417,629, Apr. 6, 1995, and Ser. No. 424,550, Jun. 5, 1995, which is a continuation-in-part of Ser. No. 377,557, Jan. 30, 1995, abandoned, which is a continuation-in-part of Ser. No. 344,184, Nov. 23, 1994, abandoned, and Ser. No. 344,190, Nov. 23, 1994, abandoned, said Ser. No. 344,185, and Ser. No. 344,190, each is a continuation-in-part of Ser. No.283,314, Jul. 29, 1994, abandoned, which is a continuation-in-part of Ser. No. 242,654, May 13, 1994, abandoned, which is a continuation-in-part of Ser. No. 196,030, Feb. 14, 1994, abandoned.

[51] Int. Cl.$^6$ .......... A61K 39/12; G01N 33/576
[52] U.S. Cl. .......... 424/189.1; 435/5; 436/518; 436/820; 530/324; 530/328; 530/403
[58] Field of Search ............ 435/5, 7.1; 424/184.1, 424/186.1, 189.1, 228.1; 436/501, 518, 547, 820; 514/12; 530/324, 403, 328

[56] References Cited

U.S. PATENT DOCUMENTS

| 4,743,535 | 5/1988 | Carrico . | |
|---|---|---|---|
| 4,876,187 | 10/1989 | Duck et al. . | |
| 5,275,947 | 1/1994 | Arima et al. | 435/252.33 |
| 5,399,346 | 3/1995 | Anderson et al. | 424/93.21 |
| 5,527,669 | 6/1996 | Resnick et al. | 435/5 |
| 5,576,302 | 11/1996 | Cook et al. | 514/44 |

FOREIGN PATENT DOCUMENTS

| 0318216 | 5/1989 | European Pat. Off. . |
|---|---|---|
| 9000597 | 1/1990 | WIPO . |
| 9408002 | 4/1994 | WIPO . |
| 9418217 | 8/1994 | WIPO . |
| 9532290 | 11/1995 | WIPO . |
| 9532291 | 11/1995 | WIPO . |
| 9532292 | 11/1995 | WIPO . |
| 9506266 | 5/1996 | WIPO . |

OTHER PUBLICATIONS

S. Chan et al., Journal of General Virology, 73: 1131–1141 (1992).
A.S. Muerhoff et al., "Genomic Organization of GB Viruses A and B: Two New Members of the Flaviviridae Associated with GB Agent Hepatitis", *Journal Of Virology*, vol. 69, No. 9, (1995), pp. 5621–5630.
T. Gura, "Antisense Has Growing Pains", *Science*, vol. 270, (1995), pp. 575–577.
D. Brown, "Gene Therapy 'Oversold' by Researchers, Journalists", *Washington Post*, (Dec. 8, 1995), pp. 1 & A22.
Choo et al., *Proc. Natl. Acad. Sci. USA*, vol. 88, pp. 2451–22455 (1991).
Okamoto et al., "Polyprotein precursor –hepatitis C virus", EMBL Sequence Accession No. S40770, Submitted Mar. 1992.
Okamoto et al., *Virology*, vol. 188, pp. 331–341 (1992).
S. K. Kuwada et al., *The American Journal of Gastroenterology*, vol. 89, No. 1, pp. 57–61 (1994).
A. S. Muerhoff et al., *Journal of Virological Methods*, vol. 62, No. 1, pp. 55–62 (1996).
A. Takamizawa et al., *Journal of Virology*, vol. 65, No. 3, pp. 1105–1113 (1991).
B. Bassam, DNA amplification fingerprinting of bacteria, *Applied Microbiology and Biotechnology* vol. 38: pp. 70–76 (1992).
G. Caetano–Anolles et al., DNA Amplification Fingerprinting of Using Very Short Aribitrary Oligonucleotide Primers, *Biotechnology* vol. 9: pp. 553–557 (1991).
J. Welsh et al., Fingerprintinggenomes using PCR with arbitrary primers*, *Acids Research* vol. 20 No. 19: pp. 4965–4970.
J. Williams et al., DNA polymorphisms amplified by arbitrary primers are useful as genetic markers, *Nucleic Acids Research* vol. 18 No. 22: pp. 6531–6535 (1990).
P. Liang et al., Differential Display of Eukaryotic Messenger RNA by Means of the Polymerase Chain Reaction, *Science* vol. 257: pp. 967–971 (1992).
P. Liang et al., Distribution and cloning of eukaryotic mRNAs by means of diferential display: refinements and optimization, *Nucleic Acids Research* vol. 21 No. 14: pp. 3269–3275 (1993).
J. Simons et al., Indentification of two flavivirus–like genomes in the GB Hepatitis agent, *Ppoc. Natl. Acad. Sci. USA* vol. 92: pp. 3401–3405 (1995).
J. Simons et al., Isolation of novel virus–like sequences associated with human hepatitis, *Nature Medicine* vol. 1 No. 6: pp. 564–568 (1995).
G. Schlauder et al., Molecular and Serologic Analysis in the Transmission of the GB Hepatitis Agents, *Journal of Medical Virology* vol. 46: pp. 81–90 (1995).
M. Yoshiba et al., Detection of the GBV–C hepatitis virus genome in serum from patients with fulminant hepatitis of unknown aetiology, *The Lancet* vol. 346: pp. 1131–1132 (1995).

(List continued on next page.)

*Primary Examiner*—Donna Wortman
*Attorney, Agent, or Firm*—Dianne Casuto; Priscilla E. Porembski

[57] ABSTRACT

Hepatitis GB Virus (HGBV) synthetic peptides useful for a variety of diagnostic and therapeutic applications, kits for using the HGBV nucleic acid or amino acid sequences and antibodies which specifically bind to HGBV. Also provided are methods for producing antibodies, polyclonal or monoclonal, from the HGBV peptides.

15 Claims, No Drawings

OTHER PUBLICATIONS

J. Linnen et al., Molecular Cloning and Disease Association of Heatitis G Virus: A Transfusion–Transmissible Agent, *Science* vol. 271: pp. 505–508 (1996).

A. Zuckerman, Tnew GB hepatitis viruses, *The Lancet* vol. 345: pp. 1453–1455 (1995).

L. Altman, Three Newly Discovered Viruses May Cause Unexplained Hepatitis, *The New York Times Medical Science*, Apr. 11, 1995.

L. Altman, Newly Found Viruses May Cause Hepatitis, *The New York Times Medical Science*, Apr. 10, 1995.

T. Leary et., Sequence and Genomic Organization of GBV–C: A novel Member of the Flavivirdae Associated With Human Non–A–E Hepetitis, *Journal of Medical Virology* vol. 48: pp. 80–87 (1996).

G. Caetano–Anolles et al., DNA Amplification Fingerprinting Using Arbitrary Oligonucleotide Primers, *Applied Biochemistry and Biotechnology* vol. 42: pp. 189–200 (1993).

S. Friedman et al., The core element of the EcoRII methylase as defined by protease digestion and deletion analysis, *Nucleic Acids Research* vol. 19 No. 19: p. 5403–5408 (1991).

A. Rosenthal et al., Genomic walking and sequencing by oligo–cassette mediated polymerase chain reaction, *Nucleic Acids Research* vol. 18 No 10: p. 3095–3096 (1990).

A. Akowitz, Protected endogenous retroviral sequences copurify with infectivity in experimental Creutzfeldt–Jakob disease, *Archives of Virology* vol. 130: p. 301–316 (1993).

Non–A, Non–B?, *The Lancet* vol. 2: pp. 64–65 (1975).

F. Hollinger, Non–A, Non–B Hepatitis Viruses, *Virology* : pp. 2239–2273 (1990).

J. Dienstag, Non–A, Non–B Hepatitis I. Recongnition, Epidemiology, and Clinical Features, *Gastroenterology* vol. 85 No. 2: pp. 439–462 (1983).

J. Strauss et al., Structure and Function of the Flavivirus and Pestivirus Genomes, *Viral Hepatitis and Liver Disease*: pp. 333–344 (1990).

H. Alter et al., Posttransfusion Hepatitis After Exclusion of Commercial and Hepatitis–B Antigen–Positive Donors, *Annals of Internal Medicine* vol. 77 No. 5: p. 691–699 (1972).

H. Alter et al., Clinical and Serological Analysis of Transfusion–Associated Hepatitis, *The Lancet*: pp. 838–841 (1975).

S. Feinstone et al., Transfusion–Associated Hepatitis Not Due To Viral Hepatitis Type A or B, *The New England Journal of Medicine* vol. 292 No. 15: pp. 767–770 (1975).

S. Feinstone et al., Hepatitis A: Detection by Immune Electron Microscopy of a Viruslike Antigen Associated with Acute Illness, *Science* vol. 182: p. 1026–1028 (1973).

E. Tabor et al., Lack of Susceptibility of Marmosets to Human Non–A, Non–B Hepatitis, *The Journal of Infectious Diseases* vol. 140 No. 5: pp. 794–797 (1979).

E. Fagan et al., Toga Virus–Like Particles in Acute Liver Failure Attributed to Sporadic Non–A, Non–B Hepatitis and Recurrence After Liver Transplantation, *Journal of Medical Virology* vol. 38: pp. 71–77 (1992).

J. Dienstage, Virus particles in marmoset hepatitis, *Nature* vol. 267: pp. 729–730 (1977).

F. Deinhardt et al., Hepatitis in Marmosets, *The Journal of Infectious Diseases* vol. 121 No. 3: pp. 351–354 (1970).

F. Deinhardt et al., The Mythology of Various Hepatitis A Virus Isolates, *International Symposium on Viral Hepatitis*: pp. 390–404 (1975).

M. Alter et al., The Natural History of Community–Acquired Hepatitis C in the United States, *The New England Journal of Medicine* vol. 327 No. 27: pp. 1899–1905 (1992).

R. Gibbs, Polymerase chain reaction techniques, *Analytical Biotechnology*: pp. 69–75 (1991).

F. Deinhardt et al., Hepatitis in marmosets, *The American Journal of the Medical Sciences* vol. 270: p. 73–80 (1975).

S. Kalter, Comparison of Infectivity of Human Non–A/Non–B Hepatitis and the GB Hepatitis Agent in Marmosets, *Viral and Immunological Diseases in Nonhuman Primates*;: pp. 221–224 (1983).

E. Tabor et al., Transmission of Human Non–A, Non–B Hepatitis to Chimpanzees following Failure to Transmit GB Agent Hepatitis, *Journal of Medical Virology*: pp. 103–108 (1980).

D. Bradley et al., Posttransfusion Non–A, Non–B Hepatitis: Physicochemical Properties of Two Distinct Agents, *The Journal of Infectious Disease* vol. 148 No. 2: pp. 254–265 (1983).

J. Deinstag, Virus–like particles and GB agent hepatitis, *Nature* vol. 264: pp. 260–261 (1976).

P. Karayiannis et al., Studies of GB Hepatitis Agent in Tamarins, *Hepatology* vol. 9 No. 2: pp. 186–192 (1989).

J. Melnick, Classification of Hepatitis A Virus as Enterovirus Type 72 and of Hepatitis B Virus as Hepadnavirus Type 1, *Intervirology* vol. 18: pp. 105–106 (1982).

W. Parks et al., Characterization of Marmoset Hepatitis A Virus, *The Journal of Infectious Diseases* vol. 120 No. 5: p. 548–559 (1969).

Heptitis C virus upstanding, *The Lancet* vol. 335: pp. 1431–1432 (1990).

W. Parks et al., Attempted Isolation fo Hepatitis Viruses in Marmosets, *The Journal of Infectious Diseases* vol. 120 No. 5: 539–547 (1969).

A. Holmes et al., Specific Neutralization of Human Hepatitis Type A in Marmoset Monkeys, *Nature* vol. 243: pp. 419–420 (1973).

P. Provost et al., Physical, Chemical and Morphologic Dimensions of Human Hepatitis A Virus Strain CR326 (38578), *Proceeding of the Society for Experimental Biology and Medicine* vol. 148: pp. 532–539 (1975).

Q. Choo et al., Isolation of a cDNA Clone Derived from a Blood–Borne Non–A, Non–B Viral Hepatitis Genome, *Science* vol. 244: pp. 359–361 (1989).

J. Almeida et al., Morphology of the GB hepatitis agent, *Nature* vol. 261: pp. 608–609 (1976).

F. Deinhardt et al., Studies on the Transmission of Human Viral Heptitis to Marmoset Monkeys, *Journal of Experimental Medicine* vol. 125: pp. 673–688, Plate 81–86 (1966).

J. Dienstag, Non–A, Non–B Hepatitis. II. Experimental Transmission, Putative Virus Agents and Markers, and Prevention, *Gastroenterology* vol. 85 No. 3: pp. 743–768 (1983).

F. Hollinger et al., Transfusion–Transmitted Viruses Study: Experimental Evidence for Two Non–A, Non–B Hepatitis Agents, *Journal of Infectious Diseases* vol. 142 No. 3: pp. 400–407 ( 1980).

D. Bradley, Transmission, Etiology, and Pathogenesis of Viral Hepatitis Non–A, Non–B in Non–Human Primates, *Advances in Hepatitis Research*: pp. 268–280 (1984).

P. Yarbough et al., Hepatitis E Virus: Identification of Type–Common Epitopes, *Journal of Virology* vol. 65 No. 11: pp. 5790–5797 (1991).

H. Alter et al., Detection of Antibody to Hepatitis C Virus in Prospectively Followed Transfusion Recipients with Acute and Chronic Non–A, Non–B Hepatitis, *The New England Journal of Medicine* vol. 321 No. 22: pp. 1494–1500 (1989).

M. Alter et al., Risk Factors for Acute Non–A, Non–B Hepatitis in the United States and Association With Hepatitis C Virus Infection, *JAMA* vol. 264 No. 17: pp. 2231–2235 (1990).

J. Dienstag, Hepatitis Non–A, Non–B: C at Last, *Gastroenterology* vol. 99 No. 4: pp. 1177–1180 (1990).

G. Reyes et al., Isolation of a cDNA from the Virus Responsible for Enterically Transmitted Non–A, Non–B Hepatitis, *Science* vol. 247 : pp. 1335–1339 (1990).

G. Kuo et al., An Assay for Circulating Antibodies to a Major Etiologic Virus of Human Non–A, Non–B Hepatitis, *Science* vol. 244 : pp. 362–364 (1989).

A. Weiner et al., —Detection *of hepatitis C viral sequences in non–A, non–B hepatitis, The Lancet* vol. 335: pp. 1–3 (1990).

G. Schlauder et al., Viraemia in Egyptian children with hepatitis E virus infection, *The Lancet* vol. 341: pp. 378 (1993).

N. Lisitsyn et al., Cloning the Differences Between Two Complex Genomes, *Science* vol. 259: pp. 946–951 (1993).

V. Thiers et al., Post–transfusional anti–HCV–negative non–A non–B hepatitis (II) serological and polymerase chain reaction analysis for hepatitis C and hepatitis B viruses, *Journal of Hepatology* vol. 18: pp. 31–39 (1993).

T. Peters et al., Frequency of Hepatitis C in Acute Post-Transfusion Hepatitis After Open–Heart Surgery: A Prospective Study in 1,476 Patients, *Journal of Medical Virology* vol. 39: 139–145 (1993).

R. Purcell, *The Discovery of the Hepatitis Viruses, Gastroenterology* vol. 104 No. 4: 955–963 (1993).

G. Dawson et al., *Solid–phase enzyme–linked immunosobent assay for hepatitis E virus IgG and IgM antibodies utilizing recombinant antigens and synthetic peptides, Journal of Virological Methods* vol. 38: 175–186 (1992).

HEPATITIS GB VIRUS SYNTHETIC PEPTIDES AND USES THEREOF

This application is a continuation-in-part application of U.S. Ser. No. 08/417,629 filed Apr. 6, 1995, which is incorporated herein by reference.

This application also is a continuation-in-part application of U.S. Ser. No. 08/424,550 filed Jun. 5, 1995 which is a nationalization of P.C.T. application PCT/US95/02118 filed Feb. 14, 1995, which is a continuation-in-part application of U.S. Ser. No. 08/377,557 filed Jan. 30, 1995, abandoned, which is a continuation-in-part of U.S. Ser. No. 08/344,185 filed Nov. 23, 1994, abandoned, and U.S. Ser. No. 08/344,190 filed Nov. 23, 1994, abandoned, which are each continuation-in-part applications of Ser. No. 08/283,314 filed Jul. 29, 1994, abandoned, which is a continuation-in-part application of U.S. Ser. No. 08/242,654, filed May 13, 1994, abandoned, which is a continuation-in-part application of U.S. Ser. No. 08/196,030 filed Feb. 14, 1994, abandoned, all of which enjoy common ownership and each of which is incorporated herein by reference.

BACKGROUND OF THE INVENTION

This invention relates generally to synthetic peptides derived from a group of infectious viral agents causing hepatitis in man, and more particularly, relates to synthetic peptides which specifically bind to hepatitis GB Virus (HGBV), and uses for these synthetic peptides.

Hepatitis is one of the most important diseases transmitted from a donor to a recipient by transfusion of blood products, organ transplantation and hemodialysis; it also can be transmitted via ingestion of contaminated food stuffs and water, and by person to person contact. Viral hepatitis is known to include a group of viral agents with distinctive viral genes and modes of replication, causing hepatitis with differing degrees of severity of hepatic damage through different routes of transmission. In some cases, acute viral hepatitis is clinically diagnosed by well-defined patient symptoms including jaundice, hepatic tenderness and an elevated level of liver transaminases such as aspartate transaminase (AST), alanine transaminase (ALT) and isocitrate dehydrogenase (ISD). In other cases, acute viral hepatitis may be clinically inapparent. The viral agents of hepatitis include hepatitis A virus (HAV), hepatitis B virus (HBV), hepatitis C virus (HCV), hepatitis delta virus (HDV), hepatitis E virus (HEV), Epstein-Barr virus (EBV) and cytomegalovirus (CMV).

Although specific serologic assays available by the late 1960's to screen blood donations for the presence of HBV surface antigen (HBsAg) were successful in reducing the incidence of post-transfusion hepatitis (PTH) in blood recipients, PTH continued to occur at a significant rate. H. J. Alter et al., *Ann. Int. Med.* 77:691–699 (1972); H. J. Alter et al., *Lancet* ii:838–841 (1975). Investigators began to search for a new agent, termed "non-A, non-B hepatitis" (NANBH), that caused viral hepatitis not associated with exposure to viruses previously known to cause hepatitis in man (HAV, HBV, CMV and EBV). See, for example, S. M. Feinstone et al., *New Engl. J. Med.* 292:767–770 (1975); Anonymous editorial, *Lancet* ii:64–65 (1975); F. B. Hollinger in B. N. Fields and D. M. Knipe et al., *Virology*, Raven Press, New York, pp. 2239–2273 (1990).

Several lines of epidemiological and laboratory evidence have suggested the existence of more than one parenterally transmitted NANB agent, including multiple attacks of acute NANBH in intravenous drug users; distinct incubation periods of patients acquiring NANBH post-transfusion; the outcome of cross-challenge chimpanzee experiments; the ultrastructural liver pathology of infected chimpanzees; and the differential resistance of the putative agents to chloroform. J. L. Dienstag, *Gastroenterology* 85:439–462 (1983); J. L. Dienstag, *Gastroenterology* 85:743–768 (1983); F. B. Hollinger et al., *J. Infect. Dis.* 142:400–407 (1980); D. W. Bradley in F. Chisari, ed., *Advances in Hepatitis Research*, Masson, New York, pp. 268–280 (1984); and D. W. Bradley et al., *J. Infect. Dis.* 148:254–265 (1983).

A serum sample obtained from a surgeon who had developed acute hepatitis was shown to induce hepatitis when inoculated into tamarins (Saguinus species). Four of four tamarins developed elevated liver enzymes within a few weeks following their inoculation, suggesting that an agent in the surgeon's serum could produce hepatitis in tamarins. Serial passage in various non-human primates demonstrated that this hepatitis was caused by a transmissible agent; filtration studies suggested the agent to be viral in nature. The transmissible agent responsible for these cases of hepatitis in the surgeon and tamarins was termed the "GB agent." F. Deinhardt et al., *J. Exper. Med.* 125:673–688 (1967). F. Deinhardt et al., *J. Exper. Med.*, supra; E. Tabor et al., *J. Med. Virol.* 5:103–108 (1980); R. O. Whittington et al., *Viral and Immunological Diseases in Nonhuman Primates*, Alan R. Liss, Inc., New York, pp. 221–224 (1983).

Although it was suggested that the GB agent may be an agent causing NANBH in humans and that the GB agent was not related to the known NANBH agents studied in various laboratories, no definitive or conclusive studies on the GB agent are known, and no viral agent has been discovered or molecularly characterized. F. Deinhardt et al., *Am. J. Med. Sci.* 270:73–80 (1975); and J. L. Dienstag et al., *Nature* 264:260–261 (1976). See also E. Tabor et al., *J. Med. Virol.*, supra; E. Tabor et al., *J. Infect. Dis.* 140:794–797 (1979); R. O. Whittington et al., supra; and P. Karayiannis et al., *Hepatology* 9:186–192 (1989).

Early studies indicated that the GB agent was unrelated to any known human hepatitis virus. S. M. Feinstone et al., *Science* 182:1026–1028 (1973); P. J. Provost et al., *Proc. Soc. Exp. Biol. Med.* 148:532–539 (1975); J. L. Melnick, *Intervirology* 18:105–106 (1982); A. W. Holmes et al., *Nature* 243:419–420 (1973); and F. Deinhardt et al., *Am. J. Med. Sci.*, supra. However, questions were raised regarding whether the GB agent was a virus which induced hepatitis infection in humans, or a latent tamarin virus activated by the GB serum and once activated, easily passaged to other tamarins, inducing hepatitis in them. Also, a small percentage of marmosets inoculated with GB-positive serum did not develop clinical hepatitis (4 of 52, or 7.6%), suggesting that these animals may have been naturally immune and thus, that the GB agent may be a marmoset virus. W. P. Parks et al., *J. Infect. Dis.* 120:539–547 (1969); W. P. Parks et al., *J. Infect. Dis.* 120:548–559 (1969). Morphological studies have been equivocal, with immune electron microscopy studies in one report indicating that the GB agent formed immune complexes with a size distribution of 20–22 nm and resembling the spherical structure of a parvovirus, while another study reported that immune electron microscopy data obtained from liver homogenates of GB-positive tamarins indicated that aggregates of 34–36 nm with icosahedral symmetry were detected, suggesting that the GB agent was a calici-like virus. See, for example, J. D. Almeida et al., *Nature* 261:608–609 (1976); J. L. Dienstag et al., *Nature*, supra.

Two hepatitis-causing viruses recently have been discovered and reported: HCV, which occurs primarily through parenteral transmission, and HEV, which is transmitted enterically. See, for example, Q. L. Choo et al., *Science* 244:359–362 (1989), G. Kuo et al., *Science* 244:362–364 (1989), E. P. Publication No. 0 318 216 (published May 31, 1989), G. R. Reyes et al., *Science* 247:1335–1339 (1990). HCV is responsible for a majority of PTH ascribed to the NANBH agent(s) and many cases of acute NANBH not acquired by transfusion. Anonymous editorial, *Lancet* 335:1431–1432 (1990); J. L. Dienstag, *Gastroenterology* 99:1177–1180 (1990); and M. J. Alter et al., *JAMA* 264:2231–2235 (1990).

While the detection of HCV antibody in donor samples eliminates 70 to 80% of NANBH infected blood in the blood supply system, the discovery and detection of HCV has not totally prevented the transmission of hepatitis. H. Alter et al., *New Eng. J. Med.* 321:1494–1500 (1989). Recent publications have questioned whether additional hepatitis agents may be responsible for PTH and for community acquired acute and/or chronic hepatitis that is not associated with PTH. For example, of 181 patients monitored in a prospective clinical survey conducted in France from 1988 to 1990, investigators noted a total of 18 cases of PTH. Thirteen of these 18 patients tested negative for anti-HCV antibodies, HBsAg, HBV and HCV nucleic acids. The authors speculated as to the potential importance of a non-A, non-B, non-C agent causing PTH. V. Thiers et al., *J. Hepatology* 18:34–39 (1993). Also, of 1,476 patients monitored in another study conducted in Germany from 1985 to 1988, 22 cases of documented cases of PTH were not related to infection with HBV or HCV. T. Peters et al., *J. Med. Virol.* 39:139–145 (1993).

It would be advantageous to identify and provide synthetic peptides encoding for a group of novel and unique viruses causing hepatitis, antibodies produced from these synthetic peptides which specifically bind to these viruses, and diagnostics and vaccines that employ these materials. Such materials could greatly enhance the ability of the medical community to more accurately diagnose acute and/or chronic viral hepatitis and could provide a safer blood and organ supply by detecting HGBV in these blood and organ donations.

SUMMARY OF THE INVENTION

The present invention provides a purified polypeptide derived from hepatitis GB virus (HGBV) comprising an amino acid sequence or fragment thereof wherein said sequence is characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C, wherein said polypeptide is prepared by synthetic means. The purified polypeptide is selected from the group consisting of SEQUENCE I.D. NO. 5 and 11, the group consisting of SEQUENCE I.D. No. 19, 20, 21 and 22, the group consisting of SEQUENCE I.D. NO. 23 and 24, or is SEQUENCE I.D. NO. 2.

Also provided is an antibody directed against at least one hepatitis GB virus (HGBV) epitope, wherein said antibody is produced by utilizing a polypeptide prepared by synthetic means, wherein the antibody is polyclonal or monoclonal.

An assay kit for determining the presence of hepatitis GB virus (HGBV) antigen or antibody in a test sample comprising a container containing a polypeptide possessing at least one HGBV epitope present in an HGBV antigen wherein said polypeptide is prepared by synthetic means. The polypeptide is characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C. The polypeptide can be attached to a solid phase. The polypeptide is selected from the group consisting of SEQUENCE I.D. NO. 5 and 11, the group consisting of SEQUENCE I.D. NO. 19, 20, 21, and 22, the group consisting of SEQUENCE I.D. NO. 23 and 24 or is SEQUENCE I.D. NO. 2.

The present invention also provides a kit for determining the presence of hepatitis GB virus (HGBV) antigen or antibody in a test sample comprising a container containing an antibody which specifically binds to an HGBV antigen, wherein said antigen comprises an HGBV epitope encoded by a sequence having at least about 60% sequence similarity to a sequence of HGBV and wherein said antibody is produced by utilizing a polypeptide prepared by synthetic means. The antibody can be attached to a solid phase.

A method for detecting hepatitis GB virus (HGBV) antigen in a test sample suspected of containing HGBV comprising contacting the test sample with an antibody or fragment thereof which specifically binds to at least one HGBV antigen, for a time and under conditions sufficient to allow the formation of antibody/antigen complexes; and detecting said complex containing the antibody, wherein said antibody is produced by utilizing a polypeptide prepared by synthetic means. The antibody can be attached to a solid phase. It can be a monoclonal or polyclonal antibody.

The present invention additionally provides a method for detecting hepatitis GB virus (HGBV) antibodies in a test sample suspected of containing said antibodies, comprising contacting the test sample with a probe polypeptide wherein said polypeptide contains at least one HGBV epitope comprising an amino acid sequence or fragment thereof is characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C, for a time and under conditions sufficient to allow antigen/antibody complexes to form; and detecting said complexes which contain the probe polypeptide. The probe polypeptide can be attached to a solid phase. The solid phase may be selected from the group consisting of beads, microliter wells, wells of test tube, nitrocellulose strips, magnetic beads and non-magnetic beads. The polypeptide is a synthetic peptide which encodes at least one epitope of HGBV is characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C. The sequence is characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C. The polypeptide is selected from the group consisting of SEQUENCE I.D. NO. 5 and 11, the group consisting of SEQUENCE I.D. NO. 19, 20, 21 and 22, the group consisting of SEQUENCE I.D. NO. 23 and 24 or is SEQUENCE I.D. NO. 2.

A vaccine for treatment of hepatitis GB virus (HGBV) infection comprising a pharmacologically effective dose of an immunogenic HGBV polypeptide or fragment thereof which polypeptide is characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C, in a pharmaceutically acceptable excipient, wherein said polypeptide is produced by utilizing a polypeptide prepared by synthetic means also is provided.

In addition, a method for producing antibodies to hepatitis GB virus (HGBV) comprising administering to an individual an isolated immunogenic polypeptide or fragment thereof comprising at least one HGBV epitope in an amount sufficient to produce an immune response, wherein said polypeptide is produced by utilizing a polypeptide prepared by synthetic means is provided.

A synthetic peptide encoding an epitope of hepatitis GB virus (HGBV) comprising a sequence of HGBV or fragment thereof is characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C. The polypeptide is selected from the group consisting of SEQUENCE I.D. NO. 5 and 11, the group consisting of SEQUENCE I.D. NO. 19, 20, 21 and 22, the group consisting of SEQUENCE I.D. NO. 23 and 24 or is SEQUENCE I.D. NO. 2. The synthetic polypeptide of claim 32 can be attached to a solid support.

Moreover, a diagnostic reagent comprising a polypeptide or fragment thereof derived from hepatitis GB virus (HGBV), wherein said polypeptide or fragment thereof encodes at least one epitope of HGBV and is characterized by a positive stranded RNA genome wherein said genome comprises an open reading frame (ORF) encoding a polyprotein wherein said polyprotein comprises an amino acid sequence having at least 35% identity to an amino acid sequence selected from the group consisting of HGBV-A, HGBV-B and HGBV-C, wherein said polypeptide is produced by synthetic means is provided. The polypeptide is selected from the group consisting of SEQUENCE I.D. NO. 5 and 11, the group consisting of SEQUENCE I.D. NO. 19, 20, 21 and 22, the group consisting of SEQUENCE I.D. NO. 23 and 24 or is SEQUENCE I.D. NO. 2.

DETAILED DESCRIPTION OF THE INVENTION

The present invention provides characterization of a newly ascertained etiological agents of non-A, non-B, non-C, non-D and non-E hepatitis-causing agents, collectively so-termed "Hepatitis GB Virus," or "HGBV." The present invention provides a method for determining the presence of the HGBV etiological agents, methods for obtaining the nucleic acid of this etiological agents created from infected serum, plasma or liver homogenates from individuals, either humans or tamarins, with HGBV to detect newly synthesized antigens derived from the genome of heretofore unisolated viral agents, and of selecting clones which produced products which are only found in infectious individuals as compared to non-infected individuals.

The present invention provides methods for producing a monoclonal antibody by using at least one of the synthetic peptides as the immunogen when producing the monoclonal antibody, as disclosed herein. Such a monoclonal antibody specifically binds to at least one epitope of HGBV The present invention provides kits containing reagents which can be used for the detection of the presence and/or amount of antibodies or antigens of HGBV, such reagents comprising a polypeptide containing an amino acid sequence from HGBV of about 3 to 5 or more amino acids in a suitable container. Other kits for various assay formats also are provided by the present invention as described herein.

Other aspects of the present invention include a polypeptide comprising at least one HGBV epitope attached to a solid phase and an antibody to an HGBV epitope attached to a solid phase.

The present invention also provides assays which utilize the synthetic polypeptides provided by the invention, as well as the antibodies described herein in various formats, any of which may employ a signal generating compound in the assay. Assays which do not utilize signal generating compounds to provide a means of detection also are provided. All of the assays described generally detect either antigen or antibody, or both, and include contacting a test sample with at least one reagent provided herein to form at least one antigen/antibody complex and detecting the presence of the complex. These assays are described in detail herein.

Vaccines for treatment of HGBV infection comprising an immunogenic synthetic peptide containing an HGBV epitope also are included in the present invention. An effective vaccine may make use of these immunogenic synthetic peptides (such as, a cocktail of synthetic peptides disclosed herein, as well as recombinant antigens and native viral antigens, administered simultaneously or at different times); some of these may be utilized alone and be supplemented with other representations of immunogenic epitopes at later times. Also included in the present invention is a method for producing antibodies to HGBV comprising administering to an individual an isolated immunogenic synthetic polypeptide containing an HGBV epitope in an amount sufficient to produce an immune response in the inoculated individual.

The term "Hepatitis GB Virus" or "HGBV", as used herein, collectively denotes a viral species which causes non-A, non-B, non-C, non-D, non-E hepatitis in man, and attenuated strains or defective interfering particles derived therefrom. This may include acute viral hepatitis transmitted by contaminated foodstuffs, drinking water, and the like; hepatitis due to HGBV transmitted via person to person contact (including sexual transmission, respiratory and parenteral routes) or via intravenous drug use. The methods as described herein will allow the identification of individuals who have acquired HGBV. Individually, the HGBV isolates are specifically referred to as "HGBV-A", "HGBV-B" and "HGBV-C." As described herein, the HGBV genome is comprised of RNA. Analysis of the nucleotide sequence and deduced amino acid sequence of the HGBV reveals that viruses of this group have a genome organization similar to that of the Flaviridae family. Based primarily, but not exclusively, upon similarities in genome organization, the International Committee on the Taxonomy of Viruses has recommended that this family be composed of three genera: Flavivirus, Pestivirus, and the hepatitis C group. Similarity searches at the amino acid level reveal that the hepatitis GB virus subclones have some, albeit low, sequence resemblance to hepatitis C virus. The information provided herein is sufficient to allow classification of other strains of HGBV.

Several lines of evidence demonstrate that HGBV-C is not a genotype of HCV. First, sera containing HGBV-C sequences were tested for the presence of HCV antibody. Routine detection of individuals exposed to or infected with HCV relies upon antibody tests which utilize antigens derived from three or more regions from HCV-1. These tests allow detection of antibodies to the known genotypes of HCV (See, for example, Sakamoto et al., *J. Gen. Virol.* 75:1761–1768 (1994) and Stuyver et al., *J. Gen. Virol.* 74:1093–1102 (1993). HCV-specific ELISAs failed to detect sera containing GB-C sequences in six of eight cases. Second, several human sera that were seronegative for HCV antibodies have been shown to be positive for HCV genomic RNA by a highly sensitive RT-PCR assay (Sugitani, *Lancet* 339:1018–1019 (1992). This assay failed to detect HCV RNA in seven of eight sera containing HGBV-C sequences (TABLE A). Thus, HGBV-C is not a genotype of HCV based on both serologic and molecular assays.

The alignment of a portion of the predicted translation product of HGBV-C within the helicase region with the homologous region of HGBV-A, HGBV-B, HCV-1 and additional members of the Flaviviridae, followed by phylogenetic analysis of the aligned sequences suggests that HGBV-C is more closely related to HGBV-A than to any member of the HCV group. The sequences of HGBV-C and HGBV-A, while exhibiting an evolutionary distance of 0.42, are not as divergent as HGBV-C is from HGBV-B, which shows an evolutionary distance of 0.92. Thus, HGBV-A and HGBV-C may be considered to be members of one subgroup of the GB viruses and GBV-B a member of its own subgroup. The phylogenetic analysis of the helicase sequences from various HCV isolates show that they form a much less diverged group, exhibiting a maximum evolutionary distance of 0.20. A comparison of the HCV group and the HGBV group shows a minimum evolutionary distance between any two sequences from each group of 0.69. The distance values reported hereinabove were used to generate a phylogenic tree. The relatively high degree of divergence among these viruses suggests that the GB viruses are not merely types or subtypes within the hepatitis C group; rather, they constitute their own phyletic group (or groups). Phylogenetic analysis using sequence information derived from a small portion of HCV viral genomes has been shown to be an acceptable method for the assignment of new isolates into genotypic groups (Simmonds et al., *Hepatology* 19:1321–1324 (1994). In the current analysis, the use of a 110 amino acid sequence within the helicase gene from representative HCV isolates has properly grouped them into their respective genotypes (Simmonds et al., *J. Gen. Virol.* 75:1053–1061 (1994). Therefore, the evolutionary distances shown, in all likelihood, accurately reflect the high degree of divergence between the GB viruses and the hepatitis C virus. By "identity" as used herein is meant the exact match-up of the amino acid sequence of HGBV and that of another strain(s) at the appropriate place on each genome. Also, in general, by "similarity" is meant the exact match-up of amino acid sequence of HGBV and that of another strain(s) at the appropriate place, where the amino acids are identical or possess similar chemical and/or physical properties such as charge or hydrophobicity. The programs available in the Wisconsin Sequence Analysis Package, Version 8 (available from the Genetics Computer Group, Madison, Wis., 53711), for example, the GAP program, are capable of calculating both the identity and similarity between two polynucleotide or two polypeptide sequences. Other programs for calculating identity and similarity between two sequences are known in the art.

Additionally, the following parameters are applicable, either alone or in combination, in identifying a strain of HGBV-A, HGBV-B or HGBV-C. It is expected that the overall nucleotide sequence identity of the genomes between HGBV-A, HGBV-B or HGBV-C and a strain of one of these hepatitis GB viruses will be about 45% or greater, since it is now believed that the HGBV strains may be genetically related, preferably about 60% or greater, and more preferably, about 80% or greater.

Also, it is expected that the overall sequence identity of the genomes between HGBV-A and a strain of HGBV-A at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence. Also, it is expected that the overall sequence identity of the genomes between HGBV-B and a strain of HGBV-B at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence. Also, it is expected that the overall sequence identity of the genomes between HGBV-C and a strain of HGBV-C at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence.

The compositions and methods described herein will allow the preparation of diagnostics and vaccines for the possible different strains of HGBV, and will have utility in screening procedures for anti-viral agents. The information will be sufficient to allow a viral taxonomist to identify other strains which fall within the species. We believe that HGBV encodes the sequences that are included herein. These sequences contain open reading frames from which an immunogenic viral epitope may be found. This epitope is unique to HGBV when compared to other known hepatitis-causing viruses. The uniqueness of the epitope may be determined by its immunological reactivity with HGBV and lack of immunological reactivity with Hepatitis A, B, C, D and E viruses. Methods for determining immunological reactivity are known in the art and include, for example, radioimmunoassay (RIA), enzyme-linked immunosorbant assay (ELISA), hemagglutination (HA), fluorescence polarization immunoassay (FPIA) and several examples of suitable techniques are described herein.

A polynucleotide "derived from" a designated sequence for example, the HGBV cDNA, or from the HGBV genome, refers to a polynucleotide sequence which is comprised of a sequence of approximately at least about 6 nucleotides, is preferably at least about 8 nucleotides, is more preferably at least about 10–12 nucleotides, and even more preferably is at least about 15–20 nucleotides corresponding, i.e., similar to or complementary to, a region of the designated nucleotide sequence. Preferably, the sequence of the region from which the polynucleotide is derived is similar to or complementary to a sequence which is unique to the HGBV genome. Whether or not a sequence is complementary to or similar to a sequence which is unique to an HGBV genome can be determined by techniques known to those skilled in the art. Comparisons to sequences in databanks, for example, can be used as a method to determine the uniqueness of a designated sequence. Regions from which sequences may be derived include but are not limited to regions encoding specific epitopes, as well as non-translated and/or non-transcribed regions.

The derived polynucleotide will not necessarily be derived physically from the nucleotide sequence of HGBV, but may be generated in any manner, including but not limited to chemical synthesis, replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use.

A "polypeptide" or "amino acid" sequence derived from a designated nucleic acid sequence or from the HGBV genome refers to a polypeptide having an amino acid sequence identical to that of a polypeptide encoded in the sequence or a portion thereof wherein the portion consists of at least 3 to 5 amino acids, and more preferably at least 8 to 10 amino acids, and even more preferably 15 to 20 amino acids, or which is immunologically identifiable with a polypeptide encoded in the sequence.

The term "synthetic peptide" as used herein means a polymeric form of amino acids of any length, which by virtue of its origin or manipulation is not associated with all or a portion of the polypeptide with which it is associated in nature or in the form of a library and/or is linked to a polynucleotide other than that to which it is linked in nature, which may be chemically synthesized by methods well-known to the routineer. These synthetic peptides are useful in various applications.

A "recombinant polypeptide" or "recombinant antigen", which terms may be used interchangeably, means at least a polypeptide of genomic, semisynthetic or synthetic origin, which by virtue of its origin or manipulation is not associated with all or a portion of the polypeptide with which it is associated in nature, or in the form of a library and/or is linked to a polynucleotide other than that to which it is linked in nature. It is not necessarily translated from a designated nucleic acid sequence of HGBV or from an HGBV genome. It usually is generated by a recombinant expression system.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, either by methylation and/or by capping, and unmodified forms of the polynucleotide.

"Purified viral polypeptide" means an HGBV polypeptide or fragment thereof which is essentially free, that is, contains less than about 50%, preferably less than about 70%, and even more preferably, less than about 90% of of cellular components with which the viral polypeptide is naturally associated. Methods for purifying are known to the routineer.

"Polypeptide" as used herein indicates a molecular chain of amino acids and does not refer to a specific length of the product. Thus, peptides, oligopeptides, and proteins are included within the definition of polypeptide. This term, however, is not intended to refer to post-expression modifications of the polypeptide, for example, glycosylations, acetylations, phosphorylations and the like.

"Recombinant host cells," "host cells," "cells," "cell lines," "cell cultures," and other such terms denoting microorganisms or higher eucaryotic cell lines cultured as unicellular entities refer to cells which can be, or have been, used as recipients for recombinant vector or other transfer DNA, and include the original progeny of the original cell which has been transfected.

The term "open reading frame" or "ORF" refers to a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences.

The term "immunologically identifiable with/as" refers to the presence of epitope(s) and polypeptide(s) which also are present in and are unique to the designated polypeptide(s), usually HGBV proteins. Immunological identity may be determined by antibody binding and/or competition in binding. These techniques are known to the routineer and also are described herein. The uniqueness of an epitope also can be determined by computer searches of known data banks, such as GenBank, for the polynucleotide sequences which encode the epitope, and by amino acid sequence comparisons with other known proteins.

As used herein, "epitope" means an antigenic determinant of a polypeptide. Conceivably, an epitope can comprise three amino acids in a spatial conformation which is unique to the epitope. Generally, an epitope consists of at least five such amino acids, and more usually, it consists of at least eight to ten amino acids. Methods of examining spatial conformation are known in the art and include, for example, x-ray crystallography and two-dimensional nuclear magnetic resonance.

A polypeptide is "immunologically reactive" with an antibody when it binds to an antibody due to antibody recognition of a specific epitope contained within the polypeptide. Immunological reactivity may be determined by antibody binding, more particularly by the kinetics of antibody binding, and/or by competition in binding using as competitor(s) a known polypeptide(s) containing an epitope against which the antibody is directed. The methods for determining whether a polypeptide is immunologically reactive with an antibody are known in the art.

As used herein, the term "immunogenic polypeptide containing an HGBV epitope" means naturally occurring HGBV polypeptides or fragments thereof, as well as polypeptides prepared by other means, for example, chemical synthesis or the expression of the polypeptide in a recombinant organism.

"Treatment" refers to prophylaxis and/or therapy.

The term "individual" as used herein refers to vertebrates, particularly members of the mammalian species and includes but is not limited to domestic animals, sports animals, primates and humans; more particularly the term refers to tamarins and humans.

The term "plus strand" (or "+") as used herein denotes a nucleic acid that contains the sequence that encodes the polypeptide. The term "minus strand" (or "−") denotes a nucleic acid that contains a sequence that is complementary to that of the "plus" strand.

"Positive stranded genome" of a virus denotes that the genome, whether RNA or DNA, is single-stranded and which encodes a viral polypeptide(s).

The term "test sample" refers to a component of an individual's body which is the source of the analyte (such as, antibodies of interest or antigens of interest). These components are well known in the art. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens; and fixed cell specimens.

After preparing the synthetic peptides, as described herein, the synthetic peptides can be used to develop unique assays as described herein to detect either the presence of antigen or antibody to HGBV. These compositions also can be used to develop monoclonal and/or polyclonal antibodies with a specific synthetic peptide which specifically bind to the immunological epitope of HGBV which is desired by the routineer. Also, it is contemplated that at least one synthetic peptide of the invention can be used to develop vaccines by following methods known in the art.

It is contemplated that the reagent employed for the assay can be provided in the form of a test kit with one or more containers such as vials or bottles, with each container containing a separate reagent such as a monoclonal antibody, or a cocktail of monoclonal antibodies, or a polypeptide employed in the assay. Other components such as buffers, controls, and the like, known to those of ordinary skill in art, may be included in such test kits.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances, haptens, antibodies, and combinations thereof. As a member of a specific binding pair, the analyte can be detected by means of naturally occurring specific binding partners (pairs) such as the use of intrinsic factor protein as a member of a specific binding pair for the determination of Vitamin B 12, the use of folate-binding protein to determine folic acid, or the use of a lectin as a member of a specific binding pair for the determination of a carbohydrate. The analyte can include a protein, a peptide, an amino acid, a nucleotide target, and the like.

The present invention provides assays which utilize specific binding members. A "specific binding member," as used herein, is a member of a specific binding pair. That is, two different molecules where one of the molecules through chemical or physical means specifically binds to the second molecule. Therefore, in addition to antigen and antibody specific binding pairs of common immunoassays, other specific binding pairs can include biotin and avidin, carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, antibodies and antibody fragments, both monoclonal and polyclonal, and complexes thereof, including those formed by recombinant DNA molecules. The term "hapten", as used herein, refers to a partial antigen or non-protein binding member which is capable of binding to an antibody, but which is not capable of eliciting antibody formation unless coupled to a carrier protein.

A "capture reagent", as used herein, refers to an unlabeled specific binding member which is specific either for the analyte as in a sandwich assay, for the indicator reagent or analyte as in a competitive assay, or for an ancillary specific binding member, which itself is specific for the analyte, as in an indirect assay. The capture reagent can be directly or indirectly bound to a solid phase material before the performance of the assay or during the performance of the assay, thereby enabling the separation of immobilized complexes from the test sample.

"Solid phases" ("solid supports") are known to those in the art and include the walls of wells of a reaction tray, test tubes, polystyrene beads, magnetic beads, nitrocellulose strips, membranes, microparticles such as latex particles, sheep (or other animal) red blood cells, Duracytes® (derviatized red blood cells, available from Abbott Laboratories, Abbott Park, Ill.) and others. The "solid phase" is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and Duracytes® are all suitable examples. Suitable methods for immobilizing peptides on solid phases include ionic, hydrophobic, covalent interactions and the like. A "solid phase," as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, Duracytes® and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. All of the materials may be used in suitable shapes, such as films, sheets, or plates, or they may be coated onto or bonded or laminated to appropriate inert carriers, such as paper, glass, plastic films, or fabrics. The porous structure of nitrocellulose has excellent absorption and adsorption qualities for a wide variety of reagents including monoclonal antibodies. Nylon also possesses similar characteristics and also is suitable. It is contemplated that such porous solid supports described hereinabove are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage of the antigen or antibody to the support. The irreversible binding of the antigen or antibody is obtained, however, in general, by adsorption on the porous material by poorly understood hydrophobic forces. Suitable solid supports also are described in U.S. patent application Ser. No. 227,272, now U.S. Pat. No. 5,075,077.

The "indicator reagent" comprises a "signal generating compound" (label) which is capable of generating and generates a measurable signal detectable by external means conjugated (attached) to a specific binding member for HGBV. "Specific binding member" as used herein means a member of a specific binding pair. That is, two different molecules where one of the molecules through chemical or physical means specifically binds to the second molecule. In addition to being an antibody member of a specific binding pair for HGBV, the indicator reagent also can be a member of any specific binding pair, including either hapten-anti-hapten systems such as biotin or anti-biotin, avidin or biotin, a carbohydrate or a lectin, a complementary nucleotide sequence, an effector or a receptor molecule, an enzyme cofactor and an enzyme, an enzyme inhibitor or an enzyme, and the like. An immunoreactive specific binding member can be an antibody, an antigen, or an antibody/antigen complex that is capable of binding either to HGBV as in a sandwich assay, to the capture reagent as in a competitive assay, or to the ancillary specific binding member as in an indirect assay.

The various "signal generating compounds" (labels) contemplated include chromagens, catalysts such as enzymes, luminescent compounds such as fluorescein and rhodamine, chemiluminescent compounds such as dioxetanes, acridiniums, phenanthridiniums and luminol, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

Other embodiments which utilize various other solid phases also are contemplated and are within the scope of this invention. For example, ion capture procedures for immobilizing an immobilizable reaction complex with a negatively charged polymer, described in co-pending U.S. patent application Ser. No. 150,278, abandoned, corresponding to EP publication 0326100 and U.S. patent application Ser. No. 375,029, abandoned, (EP publication no. 0406473), can be employed according to the present invention to effect a fast solution-phase immunochemical reaction. An immobilizable immune complex is separated from the rest of the reaction mixture by ionic interactions between the negatively charged poly-anion/immune complex and the previously treated, positively charged porous matrix and detected by using various signal generating systems previously described, including those described in chemiluminescent signal measurements as described in co-pending U.S. patent application Ser. No.921,979, abandoned, corresponding to EPO Publication No. 0 273,115.

Also, the methods of the present invention can be adapted for use in systems which utilize microparticle technology including in automated and semi-automated systems wherein the solid phase comprises a microparticle (magnetic or non-magnetic). Such systems include those described in pending U.S. patent applications Ser. Nos. 425,651 and 425,643, which correspond to published EPO applications Nos. EP 0 425 633 and EP 0 424 634, now U.S. Pat. Nos. 5,244,630 and 5,089,424, respectively.

The use of scanning probe microscopy (SPM) for immunoassays also is a technology to which the monoclonal antibodies of the present invention are easily adaptable. In scanning probe microscopy, in particular in atomic force microscopy, the capture phase, for example, at least one of the monoclonal antibodies of the invention, is adhered to a solid phase and a scanning probe microscope is utilized to detect antigen/antibody complexes which may be present on the surface of the solid phase. The use of scanning tunnelling microscopy eliminates the need for labels which normally must be utilized in many immunoassay systems to detect antigen/antibody complexes. The use of SPM to monitor specific binding reactions can occur in many ways. For example, one member of a specific binding partner (analyte specific substance which is the monoclonal antibody of the invention) is attached to a surface suitable for scanning. The attachment of the analyte specific substance may be by adsorption to a test piece which comprises a solid phase of a plastic or metal surface, following methods known to those of ordinary skill in the art. Or, covalent attachment of a specific binding partner (analyte specific substance) to a test piece which test piece comprises a solid phase of derivatized plastic, metal, silicon, or glass may be utilized. Covalent attachment methods are known to those skilled in the art and include a variety of means to irreversibly link specific binding partners to the test piece. If the test piece is silicon or glass, the surface must be activated prior to attaching the specific binding partner. Also, polyelectrolyte interactions may be used to immobilize a specific binding partner on a surface of a test piece by using techniques and chemistries described by pending U.S. patent applications Ser. No. 150,278, filed Jan. 29, 1988, abandoned, and Ser. No. 375,029, filed Jul. 7, 1989, abandoned. The preferred method of attachment is by covalent means. Following attachment of a specific binding member, the surface may be further treated with materials such as serum, proteins, or other blocking agents to minimize non-specific binding. The surface also may be scanned either at the site of manufacture or point of use to verify its suitability for assay purposes. The scanning process is not anticipated to alter the specific binding properties of the test piece.

Various other assay formats may be used, including "sandwich" immunoassays and probe assays. For example, the monoclonal antibodies of the present invention can be employed in various assay systems to determine the presence, if any, of HGBV proteins in a test sample. Fragments of these monoclonal antibodies provided also may be used. For example, in a first assay format, a polyclonal or monoclonal anti-HGBV antibody or fragment thereof, or a combination of these antibodies, which has been coated on a solid phase, is contacted with a test sample which may contain HGBV proteins, to form a mixture. This mixture is incubated for a time and under conditions sufficient to form antigen/antibody complexes. Then, an indicator reagent comprising a monoclonal or a polyclonal antibody or a fragment thereof, which specifically binds to an HGBV region, or a combination of these antibodies, to which a signal generating compound has been attached, is contacted with the antigen/antibody complexes to form a second mixture. This second mixture then is incubated for a time and under conditions sufficient to form antibody/antigen/ antibody complexes. The presence of HGBV antigen present in the test sample and captured on the solid phase, if any, is determined by detecting the measurable signal generated by the signal generating compound. The amount of HGBV antigen present in the test sample is proportional to the signal generated.

Alternatively, a polyclonal or monoclonal anti-HGBV antibody or fragment thereof, or a combination of these antibodies which is bound to a solid support, the test sample and an indicator reagent comprising a monoclonal or polyclonal antibody or fragments thereof, which specifically binds to HGBV antigen, or a combination of these antibodies to which a signal generating compound is attached, are contacted to form a mixture. This mixture is incubated for a time and under conditions sufficient to form antibody/ antigen/antibody complexes. The presence, if any, of HGBV proteins present in the test sample and captured on the solid phase is determined by detecting the measurable signal generated by the signal generating compound. The amount of HGBV proteins present in the test sample is proportional to the signal generated.

In another alternate assay format, one or a combination of at least two monoclonal antibodies of the invention can be employed as a competitive probe for the detection of antibodies to HGBV protein. For example, HGBV proteins, either alone or in combination, can be coated on a solid phase. A test sample suspected of containing antibody to HGBV antigen then is incubated with an indicator reagent comprising a signal generating compound and at least one monoclonal antibody of the invention for a time and under conditions sufficient to form antigen/antibody complexes of either the test sample and indicator reagent to the solid phase or the indicator reagent to the solid phase. The reduction in binding of the monoclonal antibody to the solid phase can be quantitatively measured. A measurable reduction in the signal compared to the signal generated from a confirmed negative NANB, non-C, non-D, non-E hepatitis test sample indicates the presence of anti-HGBV antibody in the test sample.

In yet another detection method, each of the monoclonal or polyclonal antibodies of the present invention can be employed in the detection of HGBV antigens in fixed tissue sections, as well as fixed cells by immunohistochemical analysis. Cytochemical analysis wherein these antibodies are labeled directly (fluorescein, colloidal gold, horseradish peroxidase, alkaline phosphatase, etc.) or are labeled by using secondary labeled anti-species antibodies (with various labels as exemplified herein) to track the histopathology of disease also are within the scope of the present invention.

In addition, these monoclonal antibodies can be bound to matrices similar to CNBr-activated Sepharose and used for the affinity purification of specific HGBV proteins from cell cultures, or biological tissues such as blood and liver such as to purify recombinant and native viral HGBV antigens and proteins.

The monoclonal antibodies of the invention can also be used for the generation of chimeric antibodies for therapeutic use, or other similar applications.

The monoclonal antibodies or fragments thereof can be provided individually to detect HGBV antigens. Combinations of the monoclonal antibodies (and fragments thereof) provided herein also may be used together as components in a mixture or "cocktail" of at least one anti-HGBV antibody of the invention with antibodies to other HGBV regions, each having different binding specificities. Thus, this cocktail can include the monoclonal antibodies of the invention which are directed to HGBV proteins and other monoclonal antibodies to other antigenic determinants of the HGBV genome.

The polyclonal antibody or fragment thereof which can be used in the assay formats should specifically bind to a specific HGBV region or other HGBV proteins used in the assay. The polyclonal antibody used preferably is of mammalian origin; human, goat, rabbit or sheep anti-HGBV polyclonal antibody can be used. Most preferably, the polyclonal antibody is rabbit polyclonal anti-HGBV antibody. The polyclonal antibodies used in the assays can be used either alone or as a cocktail of polyclonal antibodies. Since the cocktails used in the assay formats are comprised of either monoclonal antibodies or polyclonal antibodies having different HGBV specificity, they would be useful for diagnosis, evaluation and prognosis of HGBV infection, as well as for studying HGBV protein differentiation and specificity.

It is contemplated and within the scope of the present invention that the HGBV group of viruses may be detectable in assays by use of a synthetic peptides as disclosed herein, as well as, by utilizing other recombinant or native peptide that is common to all HGBV viruses. It also is within the scope of the present invention that different synthetic, recombinant or native peptides identifying different epitopes from HGBV-A, HGBV-B, HGBV-C, or yet other HGBV viruses, can be used in assay formats. In the later case, these can be coated onto one solid phase, or each separate peptide may be coated on separate solid phases, such as microparticles, and then combined to form a mixture of peptides which can be later used in assays. Such variations of assay formats are known to those of ordinary skill in the art and are discussed hereinbelow.

In another assay format, the presence of antibody and/or antigen to HGBV can be detected in a simultaneous assay, as follows. A test sample is simultaneously contacted with a capture reagent of a first analyte, wherein said capture reagent comprises a first binding member specific for a first analyte attached to a solid phase and a capture reagent for a second analyte, wherein said capture reagent comprises a first binding member for a second analyte attached to a second solid phase, to thereby form a mixture. This mixture is incubated for a time and under conditions sufficient to form capture reagent/first analyte and capture reagent/ second analyte complexes. These so-formed complexes then are contacted with an indicator reagent comprising a member of a binding pair specific for the first analyte labeled with a signal generating compound and an indicator reagent comprising a member of a binding pair specific for the second analyte labeled with a signal generating compound to form a second mixture. This second mixture is incubated for a time and under conditions sufficient to form capture reagent/first analyte/indicator reagent complexes and capture reagent/second analyte/indicator reagent complexes. The presence of one or more analytes is determined by detecting a signal generated in connection with the complexes formed on either or both solid phases as an indication of the presence of one or more analytes in the test sample. In this assay format, proteins derived from human expression systems may be utilized as well as monoclonal antibodies produced from the proteins derived from the mammalian expression systems as disclosed herein. Such assay systems are described in greater detail in pending U.S. patent application Ser. No. 07/574,821 entitled Simultaneous Assay for Detecting One Or More Analytes, which corresponds to EP Publication No. 0473065.

In yet other assay formats, synthetic peptides may be utilized to detect the presence of anti-HGBV in test samples. For example, a test sample is incubated with a solid phase to which at least one synthetic peptide has been attached. These are reacted for a time and under conditions sufficient to form antigen/antibody complexes. Following incubation, the antigen/antibody complex is detected. Indicator reagents may be used to facilitate detection, depending upon the assay system chosen. In another assay format, a test sample is contacted with a solid phase to which a synthetic peptide produced as described herein is attached and also is contacted with a monoclonal or polyclonal antibody specific for the protein, which preferably has been labeled with an indicator reagent. After incubation for a time and under conditions sufficient for antibody/antigen complexes to form, the solid phase is separated from the free phase, and the label is detected in either the solid or free phase as an indication of the presence of HGBV antibody. Other assay formats utilizing the proteins of the present invention are contemplated. These include contacting a test sample with a solid phase to which at least one antigen from a first source has been attached, incubating the solid phase and test sample for a time and under conditions sufficient to form antigen/antibody complexes, and then contacting the solid phase with a labeled antigen, which antigen is derived from a second source different from the first source. For example, a recombinant protein to a particular HGBV antigen derived from a first source such as *E. coli* is used as a capture antigen on a solid phase, a test sample is added to the so-prepared solid phase, and a polypeptide which specifically binds to the analyte of the test sample, derived from a different source (i.e., a synthetic peptide of the invention) is utilized as a part of an indicator reagent. Likewise, combinations of a recombinant antigen on a solid phase and synthetic peptide in the indicator phase also are possible. Any assay format which utilizes an antigen specific for HGBV from a first source as the capture antigen and an antigen specific for HGBV from a different second source are contemplated. Thus, various combinations of recombinant antigens, as well as the use of synthetic peptides disclosed herein, purified viral proteins, and the like, are within the scope of this invention. Assays such as this and others are described in U.S. Pat. No. 5,254,458, which enjoys common ownership and is incorporated herein by reference.

Other assay systems which utilize an antibody (polyclonal, monoclonal or naturally-occurring) which specifically binds HGBV viral particles or sub-viral particles housing the viral genome (or fragments thereof) by virtue of a contact between the specific antibody and the viral protein (peptide, etc.). This captured particle then can be analyzed by methods such as LCR or PCR to determine whether the viral genome is present in the test sample. Test samples which can be assayed according to this method include blood, liver, sputum, urine, fecal material, saliva, and the like. The advantage of utilizing such an antigen capture amplification method is that it can separate the viral genome from other molecules in the test specimen by use of a specific antibody. Such a method has been described in pending U.S. patent application Ser. No. 08/141,429.

While the present invention discloses the preference for the use of solid phases, it is contemplated that the reagents such as antibodies, proteins and peptides of the present invention can be utilized in non-solid phase assay systems. These assay systems are known to those skilled in the art, and are considered to be within the scope of the present invention.

Materials and Methods

General Techniques

Conventional and well-known techniques and methods in the fields of molecular biology, microbiology, recombinant DNA and immunology are employed in the practice of the invention unless otherwise noted. Such techniques are explained and detailed in the literature. See, for example, J. Sambrook et al., *Molecular Cloning: A Laboratory Manual,* 2nd edition, Cold Spring Harbor Press, Cold Spring Harbor, N.Y. (1989); D. N. Glover, ed., *DNA Cloning, Volumes I and II* (1985); M. J. Gait ed., *Oligonucleotide Synthesis,* (1984); B. D. Hames et al., eds., *Nucleic Acid Hybridization,* (1984); B. D. Hames et al., eds., *Transcription and Translation,* (1984); R. I. Freshney ed., *Animal Cell Culture,* (1986); *Immobilized Cells and Enzymes,* IRL Press (1986); B. Perbal, *A Practical Guide to Molecular Cloning,* (1984); the series, *Methods in Enzymology,* Academic Press, Inc., Orlando, Fla.; J. H. Miller et al., eds., *Gene Transfer Vectors For Mammalian Cells,* Cold Spring Harbor Laboratory, Cold Spring Harbor, N.Y. (1987); Wu et al., eds., *Methods in Enzymology,* Vol. 154 and 155; Mayer et al., eds., *Immunological Methods In Cell and Molecular Biology,* Academic Press, London (1987); Scopes, *Protein Purification: Principles and Practice,* 2nd ed., Springer-Verlag, N.Y.; and D. Weir et al., eds., *Handbook Of Experimental Immunology,* Volumes I–IV (1986); N. Lisitisyn et al., *Science* 259:946–951 (1993).

The sequences (and their complements) retrieved from the HGBV sequence as provided herein, and the sequences or any portion thereof, can be prepared using synthetic methods or by a combination of synthetic methods with retrieval of partial sequences using methods similar to those described herein.

Preparation of Antigenic Polypeptides and Conjugation With Solid Phase

An antigenic region or fragment of a polypeptide generally is relatively small, usually about 8 to 10 amino acids or less in length. Fragments of as few as 5 amino acids may characterize an antigenic region. These segments may correspond to regions of HGBV antigen. By using the HGBV genomic or cDNA sequences as a basis, nucleic acid sequences encoding short segments of HGBV polypeptides can be expressed recombinantly either as fusion proteins or as isolated polypeptides. These short amino acid sequences also can be obtained by chemical synthesis. The small chemically synthesized polypeptides may be linked to a suitable carrier molecule when the synthesized polypeptide provided is correctly configured to provide the correct epitope but too small to be antigenic. Linking methods are known in the art and include but are not limited to using N-succinimidyl-3-(2-pyrdylthio)propionate (SPDP) and succinimidyl 4-(N-maleimidomethyl)cyclohexane-1-carboxylate (SMCC). Polypeptides lacking sulfhydryl groups can be modified by adding a cysteine residue. These reagents create a disulfide linkage between themselves and peptide cysteine residues on one protein and an amide linkage through the epsilon-amino on a lysine, or other free amino group in the other. A variety of such disulfide/amide-forming agents are known. Other bifunctional coupling agents form a thioester rather than a disulfide linkage. Many of these thio-ether-forming agents are commercially available and are known to those of ordinary skill in the art. The carboxyl groups can be activated by combining them with succinimide or 1-hydroxyl-2-nitro-4-sulfonic acid, sodium salt. Any carrier which does not itself induce the production of antibodies harmful to the host can be used. Suitable carriers include proteins, polysaccharides such as latex functionalized sepharose, agarose, cellulose, cellulose beads, polymeric amino acids such as polyglutamic acid, polylysine, amino acid copolymers and inactive virus particles, among others. Examples of protein substrates include serum albumins, keyhole limpet hemocyanin, immunoglobulin molecules, thyroglobulin, ovalbumin, tetanus toxoid, and yet other proteins known to those skilled in the art.

Preparation of Hybrid Particle Immunogens Containing HGBV Epitopes Vaccine Preparation Vaccines may be prepared from one or more immunogenic polypeptides or nucleic acids derived from HGBV nucleic acid sequences or from the HGBV genome to which they correspond. Vaccines may comprise recombinant polypeptides containing epitope(s) of HGBV. These polypeptides may be expressed in bacteria, yeast or mammalian cells, or alternatively may be isolated from viral preparations. It also is anticipated that various structural proteins may contain epitopes of HGBV which give rise to protective anti-HGBV antibodies. Synthetic peptides therefore also can be utilized when preparing these vaccines. Thus, polypeptides containing at least one epitope of HGBV may be used, either singly or in combinations, in HGBV vaccines. It also is contemplated that nonstructural proteins as well as structural proteins may provide protection against viral pathogenicity, even if they do not cause the production of neutralizing antibodies.

Considering the above, multivalent vaccines against HGBV may comprise one or more structural proteins, and/or one or more nonstructural proteins. These vaccines may be comprised of, for example, recombinant HGBV polypeptides and/or polypeptides isolated from the virions and/or synthetic peptides. These immunogenic epitopes can be used in combinations, i.e., as a mixture of recombinant proteins, synthetic peptides and/or polypeptides isolated from the virion; these may be administered at the same or different time. Additionally, it may be possible to use inactivated HGBV in vaccines. Such inactivation may be by preparation of viral lysates, or by other means known in the art to cause inactivation of hepatitis-like viruses, for example, treatment with organic solvents or detergents, or treatment with formalin. Attenuated HGBV strain preparation also is disclosed in the present invention. It is contemplated that some of the proteins in HGBV may cross-react with other known viruses, and thus that shared epitopes may exist between HGBV and other viruses which would then give rise to protective antibodies against one or more of the disorders caused by these pathogenic agents. It is contemplated that it may be possible to design multiple purpose vaccines based upon this belief.

The preparation of vaccines which contain at least one immunogenic peptide as an active ingredient is known to one skilled in the art. Typically, such vaccines are prepared as injectables, either as liquid solutions or suspensions; solid forms suitable for solution in or suspension in liquid prior to injection also may be prepared. The preparation may be emulsified or the protein may be encapsulated in liposomes. The active immunogenic ingredients often are mixed with pharmacologically acceptable excipients which are compatible with the active ingredient. Suitable excipients include but are not limited to water, saline, dextrose, glycerol, ethanol and the like; combinations of these excipients in various amounts also may be used. The vaccine also may contain small amounts of auxiliary substances such as wetting or emulsifying reagents, pH buffering agents, and/or adjuvants which enhance the effectiveness of the vaccine. For example, such adjuvants can include aluminum hydroxide, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyl-L-alanyl-D-isoglutaminyl-L-alanine-2-(1'2'-dipalmitoyl-sn-glycero-3-hydroxphosphoryloxy) ethylamine (CGP 19835A, also referred to as MTP-PE), and RIBI (MPL+TDM+CWS) in a 2% squalene/TWEEN-80® emulsion. The effectiveness of an adjuvant may be determined by measuring the amount of antibodies directed against an immunogenic polypeptide containing an HGBV antigenic sequence resulting from administration of this polypeptide in vaccines which also are comprised of the various adjuvants.

The vaccines usually are administered by intravenous or intramuscular injection. Additional formulations which are suitable for other modes of administration include suppositories and, in some cases, oral formulations. For suppositories, traditional binders and carriers may include but are not limited to polyalkylene glycols or triglycerides. Such suppositories may be formed from mixtures containing the active ingredient in the range of about 0.5% to about 10%, preferably, about 1% to about 2%. Oral formulation include such normally employed excipients as, for example pharmaceutical grades of mannitol, lactose, starch, magnesium stearate, sodium saccharine, cellulose, magnesium carbonate and the like. These compositions may take the form of solutions, suspensions, tablets, pills, capsules, sustained release formulations or powders and contain about 10% to about 95% of active ingredient, preferably about 25% to about 70%.

The proteins used in the vaccine may be formulated into the vaccine as neutral or salt forms. Pharmaceutically acceptable salts such as acid addition salts (formed with free amino groups of the peptide) and which are formed with inorganic acids such as hydrochloric or phosphoric acids, or such organic acids such as acetic, oxalic, tartaric, maleic, and others known to those skilled in the art. Salts formed with the free carboxyl groups also may be derived from inorganic bases such as sodium, potassium, ammonium, calcium or ferric hydroxides and the like, and such organic bases such as isopropylamine, trimethylamine, 2-ethylamino ethanol, histidine procaine, and others known to those skilled in the art.

Vaccines are administered in a way compatible with the dosage formulation, and in such amounts as will be prophylactically and/or therapeutically effective. The quantity to be administered generally is in the range of about 5 micrograms to about 250 micrograms of antigen per dose, and depends upon the subject to be dosed, the capacity of the subject's immune system to synthesize antibodies, and the degree of protection sought. Precise amounts of active ingredient required to be administered also may depend upon the judgment of the practitioner and may be unique to each subject. The vaccine may be given in a single or multiple dose schedule. A multiple dose is one in which a primary course of vaccination may be with one to ten separate doses, followed by other doses given at subsequent time intervals required to maintain and/or to reinforce the immune response, for example, at one to four months for a second dose, and if required by the individual, a subsequent dose(s) after several months. The dosage regimen also will be determined, at least in part, by the need of the individual, and be dependent upon the practitioner's judgment. It is contemplated that the vaccine containing the immunogenic HGBV antigen(s) may be administered in conjunction with other immunoregulatory agents, for example, with immune globulins.

Preparation of Antibodies Against HGBV Epitopes

The immunogenic peptides prepared as described herein are used to produce antibodies, either polyclonal or monoclonal. When preparing polyclonal antibodies, a selected mammal (for example, a mouse, rabbit, goat, horse or the like) is immunized with an immunogenic polypeptide disclosed herein bearing at least one HGBV epitope. Serum from the immunized animal is collected after an appropriate incubation period and treated according to known procedures. If serum containing polyclonal antibodies to an HGBV epitope contains antibodies to other antigens, the polyclonal antibodies can be purified by, for example, immunoaffinity chromatography. Techniques for producing and processing polyclonal antibodies are known in the art and are described in, among others, Mayer and Walker, eds., *Immunochemical Methods In Cell and Molecular Biology,* Academic Press, London (1987). Polyclonal antibodies also may be obtained from a mammal previously infected with HGBV. An example of a method for purifying antibodies to HGBV epitopes from serum of an individual infected with HGBV using affinity chromatography is provided herein.

Monoclonal antibodies directed against HGBV epitopes also can be produced by one skilled in the art. The general methodology for producing such antibodies is well-known and has been described in, for example, Kohler and Milstein, *Nature* 256:494 (1975) and reviewed in J. G. R. Hurrel, ed., *Monoclonal Hybridoma Antibodies: Techniques and Applications,* CRC Press Inc., Boco Raton, Fla. (1982), as well as that taught by L. T. Mimms et al., *Virology* 176:604–619 (1990). Immortal antibody-producing cell lines can be created by cell fusion, and also by other techniques such as direct transformation of B lymphocytes with oncogenic DNA, or transfection with Epstein-Barr virus. See also, M. Schreier et al., Hybridoma Techniques, Scopes (1980) Protein Purification, Principles and Practice, 2nd Edition, Springer-Verlag, New York (1984); Hammerling et al., Monoclonal Antibodies and T-Cell Hybridomas (1981); Kennet et al., Monoclonal Antibodies (1980). Examples of uses and techniques of monoclonal antibodies are disclosed in U.S. patent applications Ser. Nos. 748,292; 748,563; 610,175, 648,473; 648,477; and 648,475.

Monoclonal and polyclonal antibodies thus developed, directed against HGBV epitopes, are useful in diagnostic and prognostic applications, and also, those which are neutralizing are useful in passive immunotherapy. Monoclonal antibodies especially can be used to produce anti-idiotype antibodies. These anti-idiotype antibodies are immunoglobulins which carry an "internal image" of the antigen of the infectious agent against which protection is desired. See, for example, A. Nisonoff et al., *Clin. Immunol. Immunopath.* 21:397–406 (1981), and Dreesman et al., *J. Infect. Dis.* 151:761 (1985). Techniques for raising such idiotype antibodies are known in the art and exemplified, for example, in Grych et al., *Nature* 316:74 (1985); MacNamara et al., *Science* 226:1325 (1984); and Uytdehaag et al., *J. Immunol.* 134:1225 (1985). These anti-idiotypic antibodies also may be useful for treatment of HGBV infection, as well as for elucidation of the immunogenic regions of HGBV antigens.

Immunoassay and Diagnostic Kits

Both the polypeptides which react immunologically with serum containing HGBV antibodies and composites thereof, and the antibodies raised against the HGBV specific epitopes in these polypeptides are useful in immunoassays to detect the presence of HGBV antibodies, or the presence of the virus and/or viral antigens in biological test samples. The design of these immunoassays is subject to variation, and a variety of these are known in the art; a variety of these have been described herein. The immunoassay may utilize one viral antigen, such as a polypeptide derived from any clone-containing HGBV nucleic acid sequence, or from the composite nucleic acid sequences derived from the HGBV nucleic acid sequences in these clones, or from the HGBV genome from which the nucleic acid sequences in these clones is derived. Or, the immunoassay may use a combination of viral antigens derived from these sources. It may use, for example, a monoclonal antibody directed against the same viral antigen, or polyclonal antibodies directed against different viral antigens. Assays can include but are not limited to those based on competition, direct reaction or sandwich-type assays. Assays may use solid phases or may be performed by immunoprecipitation or any other methods which do not utilize solid phases. Examples of assays which utilize labels as the signal generating compound and those labels are described herein. Signals also may be amplified by using biotin and avidin, enzyme labels or biotin anti-biotin systems, such as that described in pending U.S. patent application Ser. Nos. 608,849; 070,647; 418,981; and 687,785. Recombinant polypeptides which include epitopes from immunodominant regions of HGBV may be useful for the detection of viral antibodies in biological test samples of infected individuals. It also is contemplated that antibodies may be useful in discriminating acute from non-acute infections. Kits suitable for immunodiagnosis and containing the appropriate reagents are constructed by packaging the appropriate materials, including the polypeptides of the invention containing HGBV epitopes or antibodies directed against HGBV epitopes in suitable containers, along with the remaining reagents and materials required for the conduct of the assay, as well as suitable assay instructions.

Assay formats can be designed which utilize the synthetic peptides detailed herein. In an assay format to detect the presence of antibody against a specific analyte (for example, an infectious agent such as a virus) in a human test sample, the human test sample is contacted and incubated with a solid phase coated with at least one synthetic polypeptide). If antibodies are present in the test sample, they will form a complex with the antigenic polypeptide and become affixed to the solid phase. After the complex has formed, unbound materials and reagents are removed by washing the solid phase. The complex is reacted with an indicator reagent and allowed to incubate for a time and under conditions for second complexes to form. The presence of antibody in the test sample to the synthetic polypeptide(s) is determined by detecting the signal generated. Signal generated above a cut-off value is indicative of antibody to the analyte present in the test sample. With many indicator reagents, such as enzymes, the amount of antibody present is proportional to the signal generated. Depending upon the type of test sample, it may be diluted with a suitable buffer reagent, concentrated, or contacted with the solid phase without any manipulation ("neat"). For example, it usually is preferred to test serum or plasma samples which previously have been diluted, or concentrate specimens such as urine, in order to determine the presence and/or amount of antibody present.

In addition, more than one synthetic peptide can be used in the assay format just described to test for the presence of antibody against a specific infectious agent by utilizing synthetic peptide which specifically bind to various antigenic epitopes of the viral genome of the infectious agent under study. Thus, it may be preferred to use synthetic polypeptides which contain epitopes within a specific viral antigenic region as well as epitopes from other antigenic regions from the viral genome to provide assays which have increased sensitivity and perhaps greater specificity than using a polypeptide from one epitope. Such an assay can be utilized as a confirmatory assay. In this particular assay format, a known amount of test sample is contacted with (a) known amount(s) of at least one solid support coated with at least one recombinant protein for a time and under conditions sufficient to form synthetic peptide/antibody complexes. The complexes are contacted with known amount(s) of appropriate indicator reagent(s)s for a time and under suitable conditions for a reaction to occur, wherein the resultant signal generated is compared to a negative test sample in order to determine the presence of antibody to the analyte in the test sample. It further is contemplated that, when using certain solid phases such as microparticles, each synthetic peptide utilized in the assay can be attached to a separate microparticle, and a mixture of these microparticles made by combining the various coated microparticles, which can be optimized for each assay.

Variations to the above-described assay formats include the incorporation of synthetic peptides of different analytes attached to the same or to different solid phases for the detection of the presence of antibody to either analyte (for example, synthetic peptide specific for certain antigenic regions of one infective agent coated on the same or different solid phase with synthetic peptides or recombinant proteins specific for certain antigenic region(s) of a different infective agent, to detect the presence of either (or both) infective agents.

In yet another assay format, synthetic peptides containing antigenic epitopes are useful in competitive assays such as neutralization assays. To perform a neutralization assay, a synthetic peptide representing epitopes of an antigenic region of an infectious agent such as a virus, is solubilized and mixed with a sample diluent to a final concentration of between 0.5 to 50.0 $\mu$g/ml. A known amount of test sample (preferably 10 $\mu$l), either diluted or non-diluted, is added to a reaction well, followed by 400 $\mu$l of the sample diluent containing the recombinant polypeptide. If desired, the mixture may be preincubated for approximately 15 minutes to two hours. A solid phase coated with the synthetic peptide described herein then is added to the reaction well, and incubated for one hour at approximately 40° C. After washing, a known amount of an indicator reagent, for example, 200 $\mu$l of a peroxidase labeled goat anti-human IgG in a conjugate diluent is added and incubated for one hour at 40° C. After washing and when using an enzyme conjugate such as described, an enzyme substrate, for example, OPD substrate, is added and incubated at room temperature for thirty minutes. The reaction is terminated by adding a stopping reagent such as 1N sulfuric acid to the reaction well. Absorbance is read at 492 nm. Test samples which contain antibody to the specific polypeptide generate a reduced signal caused by the competitive binding of the peptides to these antibodies in solution. The percentage of competitive binding may be calculated by comparing absorbance value of the sample in the presence of synthetic peptide to the absorbance value of the sample assayed in the absence of a recombinant polypeptide at the same dilution. Thus, the difference in the signals generated between the sample in the presence of synthetic peptide and the sample in the absence of synthetic peptide is the measurement used to determine the presence or absence of antibody.

In another assay format, the synthetic peptide can be used in immunodot blot assay systems. The immunodot blot assay system uses a panel of purified synthetic peptide placed in an array on a nitrocellulose solid support. The prepared solid support is contacted with a sample and captures specific antibodies (specific binding member) to the synthetic peptide (other specific binding member) to form specific binding member pairs. The captured antibodies are detected by reaction with an indicator reagent. Preferably, the conjugate specific reaction is quantified using a reflectance optics assembly within an instrument which has been described in U.S. patent application Ser. No. 07/227,408 filed Aug. 2, 1988, abandoned. The related U.S. patent application Ser. No. 07/227,586, abandoned, and Ser. No. 07/227,590, now U.S. Pat. No. 5,320,808 (both of which were filed on Aug. 2, 1988) further described specific methods and apparatus useful to perform an immunodot assay, as well as U.S. Pat. No. 5,075,077 (U.S. Ser. No. 07/227,272 filed Aug. 2, 1988), which enjoys common ownership and is incorporated herein by reference. Briefly, a nitrocellulose-base test cartridge is treated with multiple antigenic polypeptides. Each polypeptide is contained within a specific reaction zone on the test cartridge. After all the antigenic polypeptides have been placed on the nitrocellulose, excess binding sites on the nitrocellulose are blocked. The test cartridge then is contacted with a test sample such that each antigenic polypeptide in each reaction zone will react if the test sample contains the appropriate antibody. After reaction, the test cartridge is washed and any antigen-antibody reactions are identified using suitable well-known reagents. As described in the patents and patent applications listed herein, the entire process is amenable to automation. The specifications of these applications related to the method and apparatus for performing an immunodot blot assay are incorporated herein by reference.

Synthetic peptides can be used in assays which employ a first and second solid support, as follow, for detecting antibody to a specific antigen of an analyte in a test sample. In this assay format, a first aliquot of a test sample is contacted with a first solid support coated with a synthetic peptide specific for an analyte for a time and under conditions sufficient to form synthetic peptide/analyte antibody complexes. Then, the complexes are contacted with an indicator reagent specific for the synthetic peptide. The indicator reagent is detected to determine the presence of antibody to the synthetic peptide in the test sample. Following this, the presence of a different antigenic determinant of the same analyte is determined by contacting a second aliquot of a test sample with a second solid support coated with a synthetic peptide specific for the second antibody for a time and under conditions sufficient to form synthetic peptide/second antibody complexes. The complexes are contacted with a second indicator reagent specific for the antibody of the complex. The signal is detected in order to determine the presence of antibody in the test sample, wherein the presence of antibody to either analyte synthetic peptide, or both, indicates the presence of anti-analyte in the test sample. It also is contemplated that the solid supports can be tested simultaneously.

The use of haptens is known in the art. It is contemplated that haptens also can be used in assays employing the synthetic peptides disclosed herein in order to enhance performance of the assay.

The present invention will now be described by way of examples, which are meant to illustrate, but not to limit, the spirit and scope of the invention.

EXAMPLES

The initial studies of the transmissibility of HGBV were performed as described in U.S. Ser. No. 08/283,314, U.S. Ser. No. 08/242,654, and U.S. Ser. No. 08/196,030, all abandoned, all of which have been incorporated previously herein by reference. Additional infectivity studies have been disclosed and described in these three preceding applications and in U.S. Ser. Nos. 08/344,185 and 08/344,190, each filed Nov. 23, 1994, both abandoned, and previously incorporated herein by reference. These previous applications also disclosed examples describing the extension of the HGBV clone sequence (generation of HGBV sequences, evidence for the existence of two HCV-like viruses in HGBV, evidence that GB-A and GB-B represent two distinct RNA species and distinct viruses, and evidence that HGBV-A and HGBV-B are members of the Flaviviridae); an example detailing the CKS-based expression vector system for expression and detection of immunogenic HGBV polypeptides, serological studies which utilized recombinant protein and its purification protocol and included a polystyrene bead coating procedure, the ELISA protocol for detection of antibodies to HGBV, and the detection of HGBV derived RNA in serum from infected individuals including humans and tamarins; an example which detailed the evidence for exposure to HGBV in human populations, including the experimental protocol used, the cutoff determinations, supplemental testing, serological data obtained with low-risk specimens, specimens tested which were from individuals considered "at risk" for hepatitis over various countries of the world, and the statistical significance of serological results obtained from testing; another example detailed additional studies which provided evidence for exposure to HGBV in human populations, including experimental protocol utilized, cutoff determination, supplemental testing, serological data obtained with low-risk specimens, serological data obtained from individuals "at risk" for hepatitis and the statistical significance of serological results; another example set forth the identification of a GB-related virus in humans, and detailed the scientific reasoning to its identification, the detailed cloning of the NS3-like region of HGBV-C, nucleotide sequences totaling 5163 bp in length, the scientific experiments which led to the conclusion that GB-C is exogenous, experiments that GB-C can be detected in additional human serum samples, experiments which detailed the PCR walking technique used to extend the HGBV-C sequence, all of which was presented as a nucleic acid sequence and a six-frame translation of the 5163 bp. These sequences are set forth in U.S. Ser. No. 08/344,190 filed Nov. 23, 1994, abandoned, which previously has been incorporated herein by reference. The sequence was obtained from clone pHGB-C clone #1, previously deposited at the A.T.C.C. and accorded A.T.C.C. Deposit No. 69711 on Nov. 8, 1994 as described in U.S. Ser. No. 08/344,190; these sequences were identified in U.S. Ser. No. 08/344,190 as SEQUENCE I.D. NO. 76 and its six possible reading frames. U.S. Ser. No. 08/377,557 filed Jan. 30, 1995, abandoned, (previously incorporated herein by reference) extended the 5163 bp sequence to a length of 8087 bp and also provided a translation of the three forward reading frames of the 8087 bp sequence. U.S. Ser. No. 08/424,550 extended the 8087 bp of HGBV-C to 9034 bp and also provided additional serological data relating to HGBV-A, HGBV-B and HGBV-C. U.S. Ser. No. 08/417,629 extended the HGBV-C sequence 88 bp, thus extending the sequence to 9122 bp, and also updated serological data of HGBV-A, HGBV-B and HGBV-C by correlating antibody detection and PCR results in Western Africa and summarizing PCR results in volunteer blood donors, I.V. drug users and non-A-E hepatitis individuals. These examples thus are meant to illustrate, but not to limit, the scope of the present invention.

Example 1

Generation of Synthetic Peptides

A. Background

Several humans and experimentally infected tamarins produced antibodies which reacted with recombinant proteins derived from the HGBV-A, HGBV-B and HGBV-C viral genomes. In order to more precisely localize the epitope(s) of immunological importance, synthetic peptides were generated. Peptide synthesis was as follows. Peptides were prepared using either of two methods: 1) peptides were synthesized on a Rainin Symphony Multiple Peptide Synthesizer using standard fMOC solid phase peptide synthesis (SPPS) on a 0.025 mmole scale with HBTU coupling chemistry by in situ activation provided by N-methylmorpholine, with 45 minute coupling times at each residue, and double coupling at predetermined residues; and 2) peptides were synthesized on an ABI 431A Peptide Synthesizer using standard fMOC solid phase peptide synthesis on a 0.25 mmole scale with activation by the HOBt/DCC method and double coupling after predetermined residues. Standard cleavage (90% trifluoroacetic acid (TFA), 2.5% each of water and ethanedithiol, 5% thioanisole, and 100 mg phenol) of the resin provided the unprotected peptide, followed by ether precipitation and washing.

B. Analysis of Synthesized Peptides

The synthesized peptides were analyzed for their amino acid composition as follows. The crude peptides from the small scale syntheses (0.025 mmole) were analyzed for their quality by C18 reverse phase high pressure liquid chromatography (HPLC) using an acetonitrile/water gradient with 0.1% TFA in each solvent. From the analytical chromatogram, the major peak from each synthesis was collected and the effluent analyzed by mass spectrometry (electrospray and/or laser desorption MS). When the observed molecular ion corresponded to the desired material, crude or purified peptide was assayed for reactivity. Purification of the peptides (small and/or large scale) was achieved using C18 reverse phase HPLC with an acetonitrile/water gradient with 0.1% TFA in each solvent. The major peak was collected and lyophilized yielding a fluffy white powder which was analyzed by mass spectrometry.

C. Mapping the Epitopes Within the 1.4 Protein

Eight overlapping 25 mers were synthesized with a six amino acid overlap (at the carboxyl end) allowing evaluation of the entire 165 amino acids from within the amino acid sequence of the NS5A region of the HGBV genome.

Example 2

ELISA Testing

A. Preparation of the Solid Phase

The utility of these epitopes was determined by coating ¼ inch polystyrene beads with each of these peptides. (More specifically, the peptides were solubilized in water or water plus glacial acetic acid and diluted to contain 10 µg/ml in phosphate buffer (pH 7.4). A total of 60 polystyrene beads was added to a scintillation vial along with 14 ml of peptide solution (10 µg/ml) and placed in an incubator at 56° C. After a two hour incubation, the liquid was aspirated and replaced with a buffer containing 0.1% TRITON-X100®/PBS. The beads were exposed to this solution for 60 minutes and then the fluid was aspirated and the beads washed two times with a PBS buffer. The beads were then exposed to 5% bovine serum albumin solution, diluted in PBS for 60 minutes at 40° C. After 60 minutes the fluid was aspirated and the beads rinsed with PBS. The beads were soaked in 5% sucrose in PBS buffer for 30 minutes. The fluids were then aspirated and the beads were air-dried.

B. ELISA procedure

An ELISA test was performed as described herein. Briefly, serum or plasma was first diluted 1:15 in specimen diluent; 10 µl of this diluted specimen was added to the well of a reaction tray along with 200 µl of specimen diluent. One antigen coated polystyrene bead was added to each well of the reaction tray and the trays were incubated at room temperature in an incubator programmed for constant agitation. After a 1 hour incubation period, the beads were washed in distilled water and a conjugate (horse radish-peroxidase labeled goat antibodies directed against human IgG) was reacted with the beads to complex with bound immunoglobulins. After a 1 hour incubation at room temperature, the beads were washed in distilled water and exposed to a substrate which produced a colored product.

C. Results

The results obtained by performing the ELISA of Example 2 with the reagents of Example 1 are summarized as follows.

i. Tamarin Serum

As noted in Example 15 of U.S. Ser. No. 08/424,550 (previously incorporated herein by reference), several of the tamarins inoculated with HGBV sera produced antibodies directed against a recombinant protein (the "CKS 1.4 recombinant protein"). These same tamarin sera were reacted with the panel of peptides shown in TABLE 1 (SEQUENCE I.D. NOS. 5, 6, 8, 9, 11, 12) in the ELISA described hereinabove. It was determined that a specific immune response was directed against the peptides referred to as SEQUENCE I.D. NO. 11.

ii. Human Serum

Several human specimens were reactive with an HGBV recombinant protein previously identified in U.S. Ser. No. 08/424,550 as the "CKS 1.4 recombinant protein". Several of these specimens were reacted with the panel of synthetic peptides (SEQUENCE I.D. NOS. 5, 6, 7, 8, 9, 10, 11, 12) in the ELISA described hereinabove. It was determined that a specific immune response was directed against the peptide referred to as SEQUENCE I.D. NO. 5. These data are shown in TABLE 2.

D. Mapping the epitopes within the CKS 2.17 protein

For the CKS 2.17 recombinant protein previously described in U.S. Ser. No. 08/424,550 (previously incorporated herein by reference), eight overlapping 25 mers were synthesized with a 5 amino acid overlap (at the carboxyl end) allowing evaluation of the entire 200 amino acids from within fragment 1.22/2.17-3 and 1.22/2.17-4.

1. The solid phase was prepared essentially as described above in Example 2(A).

2. The ELISAs were performed as described above in Example 2(B).

3. Results of Human serum. As noted in Example 15 of U.S. Ser. No. 08/424,550 (previously incorporated herein by reference), several human specimens were reactive with the CKS 2.17 recombinant protein. Several of these specimens were reacted with a panel of synthetic peptides following the ELISA set forth in Example 2(B) (SEQUENCE I.D. NOS. 13, 14, 15, 16, 17, 18, 19, 20, 21, 22). It was determined that a specific immune response was directed against the peptides referred to as SEQUENCE I.D. NOS. 19, 20, 21, 22. These data are presented in TABLE 3.

E. Epitope mapping of the CKS 4.1 protein

Three synthetic peptides were synthesized from within the CKS 4.1 protein, described in U.S. Ser. No. 08/424,550 (previously incorporated herein by reference). The first peptide comprised the first 35 amino acids of the putative core protein (1.4 protein) of GBV-B, the second comprised amino acids 27–60 of the putative core protein of HGBV-B and the third comprised amino acids 72–102 of the putative core protein of HGBV-B (SEQUENCE I.D. NOS. 23, 24, and 25, respectively).

1. The solid phase was prepared essentially as described above in Example 2(A).

2. The ELISAs were performed as described above in Example 2(B).

3. Results of Human serum. As noted in Example 15 of U.S. Ser. No. 08/424,550 (previously incorporated herein by reference), several human specimens were reactive with the CKS 4.1 recombinant protein. Several of these specimens were reacted with a panel of synthetic peptides following the ELISA procedure set forth in Example 2(B) (SEQUENCE I.D. NOS. 23, 24 and 25). It was determined that a specific immune response was directed against the peptides referred to as SEQUENCE I.D. NOS. 23 and 24. These data are presented in TABLE 4.

F. Epitope the epitopes with the CKS C.8/12 protein

Four synthetic peptides were synthesized from within the CKS C.8/12 protein, described in U.S. Ser. No. 08/424,550 (previously incorporated herein by reference). The first peptide comprised amino acids 2213–2242 of the putative NS5 protein of HGBV-C, the second comprised amino acids 2288–2317 of the putative NS5 protein of HGBV-C, the third comprised amino acids 2219–2348 of the NS5 protein of HGBV-C and the fourth comprised amino acids 2329–2358 of the NS5 protein of HGBV-C (SEQUENCE I.D. NOS. 1, 2, 3 and 4, respectively).

1. The solid phase was prepared essentially as described above in Example 2(A).

2. The ELISAs were performed as described above in Example 2(B).

3. Results of Human serum. As noted in Example 15 of U.S. Ser. No. 08/424,550 (previously incorporated herein by reference), several human specimens were reactive with the CKS C.8/12 recombinant protein. Several of these specimens were reacted with a panel of synthetic peptides following the ELISA procedure set forth in Example 2(B) (SEQUENCE I.D. NOS. 1, 2, 3 and 4). It was determined that a specific immune response was directed against the peptides referred to as SEQUENCE I.D. NO. 2. These data are presented in TABLE 5.

The data presented hereinabove thus indicate that several synthetic peptides were reactive against several test samples tested, thus indicating that these synthetic peptides have value as diagnostic reagents for detection of antibodies in individuals exposed to the HGBV viruses.

The present invention thus provides reagents and methods for determining the presence of HGBV-A, HGBV-B and HGBV-C in a test sample. It is contemplated and within the scope of the present invention that a polynucleotide or polypeptide (or fragment[s] thereof) specific for HGBV-A, HGBV-B and HGBV-C described herein, or antibodies produced from these polypeptides and polynucleotides, can be combined with commonly used assay reagents and incorporated into current assay procedures for the detection of antibody to these viruses. Alternatively, the polynucleotides or polypeptides specific for the HGBV-A, HGBV-B and HGBV-C (or fragment[s] thereof) as described herein, or antibodies produced from such polypeptides and polynucleotides (or fragment[s] thereof), can be used for detection of the HGBV-A, HGBV-B and HGBV-C viruses.

Other uses or variations of the present invention will be apparent to those of ordinary skill of the art when considering this disclosure. Therefore, the present invention is intended to be limited only by the appended claims.

TABLE 1

| | | | SAMPLES TESTED | | | | | | | | | | | |
|---|---|---|---|---|---|---|---|---|---|---|---|---|---|---|
| | | | SEQ ID # 5 | | SEQ ID # 6 | | SEQ ID # 8 SEQ ID # 5 | | SEQ ID # 9 SEQ ID # 6 | | SEQ ID # 11 | | SEQ ID # 12 | |
| | | | OD | S/N | OD | S/N | OD | S/N | OD | S/N | OD | S/N | OD | S/N |
| | | | | | | | Neg. Control | | | | | | | |
| W. Africa No. | + FOR: | S/N | 0.018 | | 0.018 | | 0.012 | | 0.013 | | 0.019 | | 0.020 | |
| 26 | CKS 1.4 | 130 | 0.029 | 1.6 | 0.084 | 4.7 | 0.035 | 2.9 | 0.022 | 1.7 | 0.051 | 2.7 | 0.083 | 4.2 |
| 314 | " | 136 | 0.015 | 0.8 | 0.023 | 1.3 | 0.012 | 1.0 | 0.016 | 1.2 | 0.020 | 1.1 | 0.020 | 1.0 |
| A8-56 | " | 28 | 0.058 | 3.2 | 0.021 | 1.2 | 0.019 | 1.6 | 0.026 | 2.0 | 0.029 | 1.5 | 0.042 | 2.1 |
| A9-12 | " | 37 | 1.470 | 81.7 | 0.030 | 1.7 | 0.034 | 2.8 | 0.044 | 3.4 | 0.044 | 2.3 | 0.130 | 6.5 |
| C1-43 | " | 22 | 0.048 | 2.7 | 0.027 | 1.5 | 0.017 | 1.4 | 0.016 | 1.2 | 0.106 | 5.6 | 0.054 | 2.7 |
| C1-16 | " | 23 | 0.017 | 0.9 | 0.019 | 1.1 | 0.013 | 1.1 | 0.027 | 2.1 | 0.024 | 1.3 | 0.035 | 1.8 |
| Tamarin 1034 pre | " | 6 | 0.008 | 0.9 | 0.012 | 0.7 | 0.006 | 0.5 | 0.005 | 0.4 | 0.013 | 0.7 | 0.011 | 0.6 |
| post 25 wk | " | 206 | 0.009 | 0.5 | 0.017 | 0.9 | 0.031 | 2.6 | 0.002 | 0.2 | 1.578 | 83.1 | 0.030 | 1.5 |
| W. Africa 418 PCR+ | " | 81 | 0.012 | 0.7 | 0.132 | 7.3 | 0.025 | 2.1 | 0.009 | 0.7 | 0.007 | 0.4 | 0.013 | 0.7 |

TABLE 2

| | | | SAMPLES TESTED | | | | | | | | 1K OPTIMIZED BEAD COATS | |
|---|---|---|---|---|---|---|---|---|---|---|---|---|
| | | | SEQ ID # 5 | SEQ ID # 6 | SEQ ID # 7 | SEQ ID # 8 | SEQ ID # 9 | SEQ ID # 10 | SEQ ID # 11 | SEQ ID # 12 | SEQ ID # 5 | SEQ ID # 11 |
| | | | aa 1–5 | aa 20–44 | a 40–65 | aa 61–85 | 81–105 | aa 101–125 | aa 121–143 | aa 141–165 | aa 1–25 | aa 121–43 |
| | | | OD  S/N | OD  S/N | OD  S/N | OD  S/N | OD  S/N | OD  S/N | OD  S/N | OD  S/N | OD  S/N | OD  S/N |
| W. AFRICA | CKS 1.4 | | | | | | | NEG. CONTROL | | | | |
| POSITIVES | S/N | WB | 0.056 | 0.049 | 0.035 | 0.024 | 0.048 | 0.037 | 0.042 | 0.050 | 0.098 | 0.088 |
| 7 | 11.35 | | 0.038  0.7 | 0.057  1.2 | 0.115  3.3 | 0.035  1.5 | 0.039  0.8 | 0.027  0.7 | 0.082  2.0 | 0.069  1.4 | 0.125  1.3 | 0.120  1.4 |
| 17 | 20.77 | | 0.854  15.3 | 0.035  0.7 | 0.047  1.3 | 0.024  1.0 | 0.023  0.5 | 0.025  0.7 | 0.028  0.7 | 0.038  0.8 | 1.840  18.8 | 0.078  0.9 |
| 21 | 12.25 | | 0.046  0.8 | 0.088  1.8 | 0.030  0.9 | 0.056  2.3 | 0.643  13.4 | 0.024  0.6 | 0.032  0.8 | 0.035  0.7 | 0.103  1.1 | 0.091  1.0 |
| 24 | 10.6 | | 0.104  1.9 | 0.037  0.8 | 0.050  1.4 | 0.042  1.8 | 0.033  0.7 | 0.040  1.1 | 0.056  1.3 | 0.073  1.5 | 0.156  1.6 | 0.085  1.0 |
| 26 | 129.9 | | 0.050  0.9 | 0.058  1.2 | 0.041  1.2 | 0.033  1.4 | 0.034  0.7 | 0.849  22.9 | 0.016  0.4 | 0.102  2.0 | 0.110  1.1 | 0.090  1.0 |
| 160 | 21.81 | | 0.039  0.7 | 0.105  2.1 | 0.052  1.5 | 0.029  1.2 | 0.035  0.7 | 0.084  2.3 | 0.044  1.0 | 0.121  2.4 | 0.138  1.4 | 0.109  1.2 |
| 43 | 12.12 | | 0.535  9.6 | 0.029  0.6 | 0.027  0.8 | 0.019  0.8 | 0.023  0.5 | 0.020  0.5 | 0.028  0.7 | 0.040  0.8 | 1.038  10.6 | 0.073  0.8 |
| 48 | 19 | | 0.872  15.6 | 0.068  1.4 | 0.042  1.2 | 0.044  1.8 | 0.057  1.2 | 0.035  0.9 | 0.073  1.7 | 0.146  2.9 | 1.546  15.8 | 0.113  1.3 |
| 59 | 35.81 | | 0.043  0.8 | 0.039  0.8 | 0.036  1.0 | 0.023  1.0 | 0.030  0.6 | 0.028  0.8 | 0.035  0.8 | 0.057  1.1 | 0.108  1.1 | 0.078  0.9 |
| 63 | 15.06 | | 0.033  0.6 | 0.016  0.3 | 0.032  0.9 | 0.029  0.6 | 0.029  0.6 | 0.086  2.3 | 0.044  1.0 | 0.052  1.0 | 0.121  1.2 | 0.103  1.2 |
| 78 | 51.83 | | 0.042  0.8 | 0.031  0.6 | 0.033  0.9 | 0.031  1.3 | 0.042  0.9 | 0.032  0.9 | 0.035  0.8 | 0.038  0.8 | 0.117  1.2 | 0.222  2.5 |
| 82 | 17.38 | | 1.480  26.4 | 0.076  1.6 | 0.056  1.6 | 0.046  1.9 | 0.033  0.7 | 0.035  0.9 | 0.039  0.9 | 0.141  2.8 | 1.560  15.9 | 0.087  1.0 |
| 100 | 17.19 | | 0.095  1.7 | 0.095  1.9 | 0.102  2.9 | 0.081  3.4 | 0.071  1.5 | 0.052  1.4 | 0.083  2.0 | 0.338  6.8 | 0.392  4.0 | 0.133  1.5 |
| 117 | 12.13 | | 0.660  11.8 | 0.058  1.2 | 0.034  1.1 | 0.029  1.2 | 0.036  0.8 | 0.039  1.1 | 0.036  0.9 | 0.123  2.5 | 1.372  14.0 | 0.123  1.4 |
| 138 | 15.79 | | 0.946  16.9 | 0.068  1.4 | 0.060  1.7 | 0.031  1.3 | 0.051  1.1 | 0.032  09 | 0.046  1.1 | 0.082  1.6 | 1.474  15.0 | 0.148  1.7 |
| 418 | 80.67 | | 0.022  0.4 | 0.089  1.8 | 0.022  0.6 | 0.013  0.5 | 0.014  0.3 | 0.014  0.4 | 0.025  0.6 | 0.025  0.5 | 0.074  0.8 | 0.066  0.8 |
| G132 | 17.59 | +++ | 0.134  2.4 | 0.042  0.9 | 0.035  1.0 | 0.038  1.6 | 0.029  0.6 | 0.030  0.8 | 0.054  1.3 | 0.076  1.5 | 0.208  2.1 | 0.116  1.3 |
| G141 | 11.55 | +++ | 0.755  13.5 | 0.049  1.0 | 0.136  3.9 | 0.033  1.4 | 0.033  0.7 | 0.044  1.2 | 0.047  1.1 | 0.065  1.3 | 0.689  7.0 | 0.089  1.0 |
| ZENOBIA | | | 1.716  30.6 | 0.053  1.1 | 0.235  6.7 | 0.038  1.6 | 0.032  0.7 | 0.024  0.6 | 0.041  1.0 | 0.057  1.1 | 3.307  33.7 | 0.127  1.4 |
| WISC 108 | | | 6.600  117.9 | 0.045  0.9 | 0.036  1.0 | 0.025  1.0 | 0.027  0.6 | 0.024  0.6 | 0.029  0.7 | 0.063  1.3 | 6.600  67.3 | 0.084  1.0 |

TABLE 3

| | | | | SAMPLES TESTED | | | | | | | | | | |
|---|---|---|---|---|---|---|---|---|---|---|---|---|---|---|
| | | | | SEQ ID # 13 | | SEQ ID # 14 | | SEQ ID # 15 | | SEQ ID # 16 | | SEQ ID # 17 | | SEQ ID # 18 | |
| | | | | OD | S/N | OD | S/N | OD | S/N | OD | S/N | OD | S/N | OD | S/N |
| 2.17 | Recom. | WSTN | | N/Cx | | | | | | | | | | | |
| Positives | S/N | BLOT | PCR | 0.025 | | 0.047 | | 0.030 | | 0.04 | | 0.042 | | 0.013 | |
| A4-41 | 26.5 | | + | 0.022 | 0.9 | 0.081 | 1.7 | 0.053 | 1.8 | 0.03 | 0.6 | 0.048 | 1.1 | 0.019 | 1.5 |
| A6-13 | 12.6 | | + | 0.035 | 1.4 | 0.127 | 2.7 | 0.039 | 1.3 | 0.16 | 4.0 | 0.045 | 1.1 | 0.023 | 1.8 |
| C1-44 | 15.1 | +/− | | 0.062 | 2.5 | 0.154 | 3.3 | 0.057 | 1.9 | 0.08 | 2.0 | 0.063 | 1.5 | 0.032 | 2.5 |
| D1-11 | 83.6 | +++ | | 0.051 | 2.0 | 0.158 | 3.4 | 0.086 | 2.9 | 0.12 | 2.9 | 0.087 | 2.1 | 0.053 | 4.1 |
| D1-41 | 1.51 | | | 0.141 | 5.6 | 0.113 | 2.4 | 0.114 | 3.8 | 0.08 | 2.0 | 0.080 | 1.9 | 0.022 | 1.7 |
| D1-26 | 19.1 | + | | 0.069 | 2.8 | 0.107 | 2.3 | 0.129 | 4.3 | 0.08 | 1.9 | 0.094 | 2.2 | 0.038 | 2.9 |
| D2-22 | 21.1 | + | | 0.033 | 1.3 | 0.107 | 2.3 | 0.067 | 2.2 | 0.03 | 0.6 | 0.030 | 0.7 | 0.010 | 0.8 |
| 148 | 18.3 | | | 0.060 | 2.4 | 0.090 | 1.9 | 0.054 | 1.8 | 0.04 | 1.0 | 0.044 | 1.0 | 0.019 | 1.5 |
| US # 57 | 16.3 | | | 0.140 | 5.6 | 0.205 | 4.4 | 0.146 | 4.9 | 0.18 | 4.7 | 0.128 | 3.0 | 0.066 | 5.1 |
| E AFRICA 342 | 55.9 | | + | 0.019 | 0.8 | 0.084 | 1.8 | 0.038 | 1.3 | 0.06 | 0.7 | 0.031 | 0.7 | 0.009 | 0.7 |

| | | | | SAMPLES TESTED | | | | | | | | | | |
|---|---|---|---|---|---|---|---|---|---|---|---|---|---|---|
| | | | | | | | | | | | | | 1K Optimized Bead Coat | |
| | | | | SEQ ID # 19 | | SEQ ID # 20 | | SEQ ID # 21 | | SEQ ID # 22 | | SEQ ID # 19 | | | |
| | | | | OD | S/N | OD | S/N | OD | S/N | OD | S/N | OD | S/N | | |
| | 2.17 | Recom. | WSTN | N/Cx | | | | | | | | | | | |
| | Positives | S/N | BLOT | PCR | 0.01 | | 0.033 | | 0.04 | | 0.05 | | 0.017 | | |
| | A4-41 | 26.5 | | + | 0.03 | 2.4 | 0.033 | 1.0 | 0.23 | 5.5 | 0.04 | 0.8 | 0.034 | 2.0 |
| | A6-13 | 12.6 | | + | 0.06 | 4.2 | 0.012 | 0.4 | 0.05 | 1.1 | 0.13 | 2.5 | 0.050 | 2.9 |
| | C1-44 | 15.1 | +/− | | 0.03 | 2.2 | 0.056 | 1.7 | 0.11 | 2.7 | 0.04 | 0.7 | 0.036 | 2.1 |
| | D1-11 | 83.6 | +++ | | 0.06 | 4.1 | 0.082 | 2.5 | 0.12 | 2.7 | 0.22 | 4.2 | 0.083 | 4.9 |
| | D1-41 | 1.51 | | | 0.06 | 4.4 | 0.067 | 2.0 | 0.09 | 2.0 | 0.03 | 0.6 | 0.048 | 2.8 |
| | D1-26 | 19.1 | + | | 0.1 | 6.9 | 0.151 | 4.6 | 0.15 | 3.5 | 0.13 | 2.5 | 0.072 | 4.2 |
| | D2-22 | 21.1 | + | | 0.03 | 2.1 | 0.032 | 1.0 | 0.12 | 2.8 | 0.02 | 0.4 | 0.028 | 1.6 |
| | 148 | 18.3 | | | 0.5 | 35.6 | 0.050 | 1.5 | 0.81 | 19.4 | 0.03 | 0.6 | 0.415 | 24.4 |
| | US # 57 | 16.3 | | | 0.1 | 7.4 | 0.129 | 3.9 | 0.22 | 5.3 | 0.09 | 1.7 | 0.072 | 4.2 |
| | E AFRICA 342 | 55.9 | | + | 0.02 | 1.2 | 0.033 | 1.0 | 0.05 | 1.1 | 0.13 | 2.4 | 0.019 | 1.1 |

TABLE 4

| | SAMPLES TESTED | | | | | |
|---|---|---|---|---|---|---|
| | SEQ ID # . | | SEQ ID # . | | SEQ ID # . | |
| | OD | S/N | OD | S/N | OD | S/N |
| | NEG. CONTROL | | | | | |
| | 0.025 | | 0.023 | | 0.021 | |
| NORMALS | | | | | | |
| 109 | 0.096 | 3.8 | 0.060 | 2.6 | 0.071 | 3.4 |
| 124 | 0.019 | 0.8 | 0.026 | 1.1 | 0.018 | 0.9 |
| 11689 | 0.060 | 2.4 | 0.362 | 15.7 | 0.057 | 2.7 |
| 34 | 0.044 | 1.8 | 0.053 | 2.3 | 0.042 | 2.0 |
| 33 | 0.052 | 2.1 | 0.054 | 2.3 | 0.045 | 2.1 |
| 107 | 0.032 | 1.3 | 0.060 | 2.6 | 0.043 | 2.0 |

TABLE 4-continued

| | SAMPLES TESTED | | | | | |
|---|---|---|---|---|---|---|
| | SEQ ID # . | | SEQ ID # . | | SEQ ID # . | |
| | OD | S/N | OD | S/N | OD | S/N |
| | NEG. CONTROL | | | | | |
| | 0.025 | | 0.023 | | 0.021 | |
| U.S. SAMPLES | | | | | | |
| 20 | 0.408 | 16.3 | 0.151 | 6.6 | 0.127 | 6.0 |
| 60 | 0.080 | 3.2 | 0.083 | 3.6 | 0.094 | 4.5 |
| 13 | 0.067 | 2.7 | 0.133 | 5.8 | 0.081 | 3.9 |
| 65 | 0.063 | 2.5 | 0.073 | 3.2 | 0.054 | 2.6 |
| 52 | 0.032 | 1.3 | 0.051 | 2.2 | 0.029 | 1.4 |
| 57 | 0.111 | 4.4 | 0.133 | 5.8 | 0.107 | 5.1 |
| 16 | 0.021 | 0.8 | 0.032 | 1.4 | 0.026 | 1.2 |
| GREEK | | | | | | |
| C 7 | 0.024 | 1.0 | 0.049 | 2.1 | 0.048 | 2.3 |
| C 11 | 0.084 | 3.4 | 0.056 | 2.4 | 0.076 | 3.6 |

TABLE 4-continued

| | SAMPLES TESTED | | | | | |
|---|---|---|---|---|---|---|
| | SEQ ID # . | | SEQ ID # . | | SEQ ID # . | |
| | OD | S/N | OD | S/N | OD | S/N |
| | NEG. CONTROL | | | | | |
| | 0.025 | | 0.023 | | 0.021 | |
| E. AFRICA | | | | | | |
| 199C | 0.030 | 1.2 | 0.037 | 1.6 | 0.033 | 1.6 |
| 235C | 0.065 | 2.6 | 0.079 | 3.4 | 0.057 | 2.7 |
| W. AFRICA A | | | | | | |
| A4 41 | 0.022 | 0.9 | 0.043 | 1.9 | 0.033 | 1.6 |
| A4 32 | 0.035 | 1.4 | 0.876 | 38.1 | 0.038 | 1.8 |
| C2 11 | 0.030 | 1.2 | 0.512 | 22.3 | 0.035 | 1.7 |
| K4 23 | 0.626 | 25.0 | 0.051 | 2.2 | 0.031 | 1.5 |
| A6 13 | 0.049 | 2.0 | 0.087 | 3.8 | 0.042 | 2.0 |
| N1 24 | 0.046 | 1.8 | 0.144 | 6.3 | 0.031 | 1.5 |
| A1 34 | 0.019 | 0.8 | 0.027 | 1.2 | 0.019 | 0.9 |
| US #14 | 0.031 | 1.2 | 0.019 | 0.8 | 0.023 | 1.1 |
| TTV | | | | | | |
| 307 | 0.012 | 0.5 | 0.023 | 1.0 | 0.014 | 0.7 |
| 384 | 0.016 | 0.6 | 0.022 | 1.0 | 0.015 | 0.7 |

TABLE 4-continued

| | SAMPLES TESTED | | | | | |
|---|---|---|---|---|---|---|
| | SEQ ID # . | | SEQ ID # . | | SEQ ID # . | |
| | OD | S/N | OD | S/N | OD | S/N |
| | NEG. CONTROL | | | | | |
| | 0.025 | | 0.023 | | 0.021 | |
| CANADIAN | | | | | | |
| 20338 | 0.041 | 1.6 | 0.037 | 1.6 | 0.037 | 1.8 |
| 20339 | 0.048 | 1.9 | 0.035 | 1.5 | 0.033 | 1.6 |
| 20340 | 0.033 | 1.3 | 0.052 | 2.3 | 0.026 | 1.2 |
| IVDU#300 | | | | | | |
| 3M | 0.054 | 2.2 | 0.042 | 1.8 | 0.046 | 2.2 |
| 6M | 0.056 | 2.2 | 0.046 | 2.0 | 0.051 | 2.4 |
| 9M | 0.065 | 2.6 | 0.051 | 2.2 | 0.049 | 2.3 |
| 12M | 0.065 | 2.6 | 0.051 | 2.2 | 0.048 | 2.3 |
| E. AFRICA 342 | 0.017 | 0.7 | 0.030 | 1.3 | 0.020 | 1.0 |
| US #47 | 0.079 | 3.2 | 0.056 | 2.4 | 0.066 | 3.1 |
| W. AFRICA | | | | | | |
| N1-21 | 0.048 | 1.9 | 0.076 | 3.3 | 0.044 | 2.1 |
| N2-21 | 0.081 | 3.2 | 0.078 | 3.4 | 0.068 | 3.2 |
| 487 | 0.052 | 2.1 | 0.061 | 2.7 | 0.041 | 2.0 |
| US RS 693 | 0.091 | 3.6 | 0.120 | 5.2 | 0.062 | 3.0 |

TABLE 5

| | | | SAMPLES TESTED | | | | | | |
|---|---|---|---|---|---|---|---|---|---|
| | | | SEQ ID#1 | | SEQ ID#2 | | SEQ ID#3 | | SEQ ID#4 | |
| | | | OD | S/N | OD | S/N | OD | S/N | OD | S/N |
| | WB | | N/C | | | | | | | |
| | | | 0.021 | | 0.016 | | 0.043 | | 0.018 | |
| | PCR | df3,4,5 | | | | | | | | |
| GREEK | | | | | | | | | | |
| 147 | + | − | 0.062 | 2.95 | 0.100 | 6.25 | 0.092 | 2.14 | 0.076 | 4.22 |
| 152 | + | − | 0.017 | 0.81 | 09.031 | 1.94 | 0.035 | 0.81 | 0.029 | 1.61 |
| 157 | + | − | 0.035 | 1.67 | 0.025 | 1.56 | 0.030 | 0.70 | 0.025 | 1.39 |
| 165 | + | +/− | 0.059 | 2.81 | 0.055 | 3.44 | 0.044 | 1.02 | 0.035 | 1.94 |
| 171 | + | − | 0.034 | 1.62 | 0.035 | 2.19 | 0.055 | 1.28 | 0.041 | 2.28 |
| 174 | + | − | 0.008 | 0.38 | 0.047 | 2.94 | 0.065 | 1.51 | 0.049 | 2.72 |
| 177 | | ++ | 0.019 | 0.90 | 0.039 | 2.44 | 0.049 | 1.14 | 0.049 | 2.72 |
| 180 | + | NT | 0.005 | 0.24 | 0.024 | 1.50 | 0.035 | 0.81 | 0.036 | 2.00 |
| 191 | + | NT | 0.015 | 0.71 | 0.062 | 3.88 | 0.068 | 1.58 | 0.053 | 2.94 |
| 197 | + | NT | 0.009 | 0.43 | 0.045 | 2.81 | 0.031 | 0.72 | 0.011 | 0.61 |
| 202 | | NT | 0.012 | 0.57 | 0.038 | 2.38 | 0.042 | 0.98 | 0.035 | 1.94 |
| 229 | + | +++ | 0.018 | 0.86 | 0.056 | 3.50 | 0.187 | 4.35 | 0.054 | 3.00 |
| EGYPT | | | | | | | | | | |
| 341A | | ++ | 0.015 | 0.71 | 0.192 | 12.00 | 0.051 | 1.19 | 0.059 | 3.28 |
| 341B | | ++ | 0.009 | 0.43 | 0.191 | 11.94 | 0.040 | 0.93 | 0.052 | 2.89 |
| U.S. | | | | | | | | | | |
| 47 | + | ++++ | 0.055 | 2.62 | 0.138 | 8.63 | 0.038 | 0.88 | 0.038 | 2.11 |
| 52 | + | +++ | 0.024 | 1.14 | 0.129 | 8.06 | 0.098 | 2.28 | 0.070 | 3.89 |
| IVDU | | | | | | | | | | |
| 300 PRE | + | ++ | 0.020 | 0.95 | 0.047 | 2.94 | 0.047 | 1.09 | 0.036 | 2.00 |
| 300 3MONTH | + | + | 0.028 | 1.33 | 0.054 | 3.38 | 0.085 | 1.98 | 0.040 | 2.22 |

What is claimed is:

1. A purified polypeptide of hepatitis GB virus (HGBV) prepared by synthetic means wherein said polypeptide is SEQUENCE I.D. NO. 5.

2. The purified polypeptide of claim 1 linked to a carrier molecule.

3. The purified polypeptide of claim 2 wherein said carrier molecule is selected from the group consisting of serum albumin, keyhole limpet hemocyanin, immunoglobulin, thyroglobulin, ovalbumin, and tetanus toxoid.

4. The purified polypeptide of claim 1 attached to a solid phase.

5. A purified polypeptide of hepatitis GB virus (HGBV) prepared by synthetic means wherein said polypeptide is s fragment having at least 8 contiguous amino acids of SEQUENCE I.D. NO. 5.

6. The purified polypeptide of claim 5 linked to a carrier molecule.

7. The purified polypeptide of claim 6 wherein said carrier molecule is selected from the group consisting of serum albumin, keyhole limpet hemocyanin, immunoglobulin, thyroglobulin, ovalbumin, and tetanus toxoid.

8. An assay kit useful for determining the presence of hepatitis GB virus (HGBV) antigen or antibody in a test sample, comprising a container containing a polypeptide prepared by synthetic means, wherein said polypeptide is SEQUENCE I.D. NO. 5.

9. The assay kit of claim 8 wherein said polypeptide is attached to a solid phase.

10. An assay kit useful for determining the presence of hepatitis GB virus (HGBV) antigen or antibody in a test sample, comprising a container containing a polypeptide prepared by synthetic means, wherein said polypeptide is a fragment having at least 8 contiguous amino acids of SEQUENCE I.D. NO. 5.

11. The assay kit of claim 10 wherein said polypeptide is attached to a solid phase.

12. A method for producing antibodies to hepatitis GB virus (HGBV) comprising administering to an individual an isolated immunogenic polypeptide produced by synthetic means, wherein said polypeptide is SEQUENCE I.D. NO. 5.

13. A method for producing antibodies to hepatitis GB virus (HGBV) comprising administering to an individual an isolated immunogenic polypeptide produced by synthetic means, wherein said polypeptide is a fragment having at least 8 contiguous amino acids of SEQUENCE I.D. NO. 5.

14. A diagnostic reagent comprising a polypeptide of hepatitis GB virus (HGBV), wherein said polypeptide is (a) produced by synthetic means, (b) SEQUENCE I.D. NO. 5, and (c) attached to a solid support.

15. A diagnostic reagent comprising a polypeptide of hepatitis GB virus (HGBV), wherein said polypeptide is (a) produced by synthetic means, (b) a fragment having at least 8 contiguous amino acids of SEQUENCE I.D. NO. 5, and (c) attached to a solid support.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:1:

```
Pro Gly Gln Ser Val Thr Ile Asp Gly Glu Arg Tyr Thr Leu Pro His
1               5                   10                  15
Gln Leu Arg Met Arg Asn Val Ala Pro Ser Glu Val Ser Ser
                20                  25                  30
```

( 2 ) INFORMATION FOR SEQ ID NO:2:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:2:

```
Glu Asp Cys Ser Thr Pro Ser Leu Cys Gly Ser Ser Arg Glu Met Pro
1               5                   10                  15
Val Trp Gly Glu Asp Ile Pro Arg Thr Pro Ser Pro Ala Leu
                20                  25                  30
```

( 2 ) INFORMATION FOR SEQ ID NO:3:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:3:

```
Ser Val Thr Glu Ser Ser Ser Asp Glu Lys Thr Leu Ser Val Thr Ser
1               5                   10                  15
Ser Gln Glu Asp Thr Pro Ser Ser Asp Ser Phe Glu Val Ile
                20                  25                  30
```

( 2 ) INFORMATION FOR SEQ ID NO:4:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:4:

```
Thr Leu Ser Val Thr Ser Ser Gln Glu Asp Thr Pro Ser Ser Asp Ser
1               5                   10                  15
```

```
    Phe Glu Val Ile Gln Glu Ser Asp Thr Ala Glu Ser Glu Glu
             20                  25                  30
```

( 2 ) INFORMATION FOR SEQ ID NO:5:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Leu Glu Ala Ile Ser Ala Gly Val Asp Thr Thr Lys Leu Pro Ala Pro
1               5                   10                  15
Ser Ile Glu Glu Val Val Val Arg Lys
             20                  25
```

( 2 ) INFORMATION FOR SEQ ID NO:6:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Glu Val Val Val Arg Lys Arg Gln Phe Arg Ala Arg Thr Gly Ser Leu
1               5                   10                  15
Thr Leu Pro Pro Pro Pro Arg Ser Val
             20                  25
```

( 2 ) INFORMATION FOR SEQ ID NO:7:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Pro Arg Ser Val Pro Gly Val Ser Cys Pro Glu Ser Leu Gln Arg Ser
1               5                   10                  15
Asp Pro Leu Glu Gly Pro Ser Asn Leu
             20                  25
```

( 2 ) INFORMATION FOR SEQ ID NO:8:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Gly Pro Ser Asn Leu Pro Ser Ser Pro Pro Val Leu Gln Leu Ala Met
1               5                   10                  15
Pro Met Pro Leu Leu Gly Ala Gly Glu
             20                  25
```

( 2 ) INFORMATION FOR SEQ ID NO:9:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
Leu Gly Ala Gly Glu Cys Asn Pro Phe Thr Ala Ile Gly Cys Ala Met
1               5                   10                  15
Thr Glu Thr Gly Gly Gly Pro Asp Asp
            20              25
```

( 2 ) INFORMATION FOR SEQ ID NO:10:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

```
Gly Gly Pro Asp Asp Leu Pro Ser Tyr Ala Pro Lys Lys Glu Val Ser
1               5                   10                  15
Glu Trp Ser Asp Gly Ser Trp Ser Thr
            20              25
```

( 2 ) INFORMATION FOR SEQ ID NO:11:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

```
Gly Ser Trp Ser Thr Thr Thr Thr Ala Ser Ser Tyr Val Thr Gly Pro
1               5                   10                  15
Pro Tyr Pro Lys Ile Arg Gly Lys Asp
            20              25
```

( 2 ) INFORMATION FOR SEQ ID NO:12:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

```
Ile Arg Gly Lys Asp Ser Thr Gln Ser Ala Pro Ala Lys Arg Pro Thr
1               5                   10                  15
Lys Lys Lys Leu Gly Lys Ser Glu Phe
            20              25
```

( 2 ) INFORMATION FOR SEQ ID NO:13:

( i ) SEQUENCE CHARACTERISTICS:
        ( A ) LENGTH: 25 amino acids (B) TYPE: amino acid
(C) STRANDEDNESS: single
(D) TOPOLOGY: linear (i i) MOLECULE TYPE: protein (x i) SEQUENCE DESCRIPTION: SEQ ID NO:13:

Leu Lys Ala Ala Asp Val Arg Arg Ala Val Arg Ala Gly Pro Thr Tyr
1               5                   10                  15
Val Gly Gly Val Pro Cys Ser Trp Ser
            20              25

(2) INFORMATION FOR SEQ ID NO:14:

(i) SEQUENCE CHARACTERISTICS:
    (A) LENGTH: 25 amino acids
    (B) TYPE: amino acid
    (C) STRANDEDNESS: single
    (D) TOPOLOGY: linear (i i) MOLECULE TYPE: protein (x i) SEQUENCE DESCRIPTION: SEQ ID NO:14:

Pro Cys Ser Trp Ser Ala Pro Cys Thr Ala Pro Ala Leu Val Tyr Arg
1               5                   10                  15
Leu Gly Gln Gly Ile Lys Ile Asp Gly
            20              25

(2) INFORMATION FOR SEQ ID NO:15:

(i) SEQUENCE CHARACTERISTICS:
    (A) LENGTH: 25 amino acids
    (B) TYPE: amino acid
    (C) STRANDEDNESS: single
    (D) TOPOLOGY: linear (i i) MOLECULE TYPE: protein (x i) SEQUENCE DESCRIPTION: SEQ ID NO:15:

Ile Lys Ile Asp Gly Ala Arg Arg Leu Leu Pro Cys Asp Leu Ala Gln
1               5                   10                  15
Gly Ala Arg His Pro Pro Val Ser Gly
            20              25

(2) INFORMATION FOR SEQ ID NO:16:

(i) SEQUENCE CHARACTERISTICS:
    (A) LENGTH: 25 amino acids
    (B) TYPE: amino acid
    (C) STRANDEDNESS: single
    (D) TOPOLOGY: linear (i i) MOLECULE TYPE: protein (x i) SEQUENCE DESCRIPTION: SEQ ID NO:16:

Pro Pro Val Ser Gly Ser Val Ala Gly Ser Gly Trp Thr Asp Glu Asp
1               5                   10                  15
Glu Arg Asp Leu Val Glu Thr Lys Ala
            20              25

(2) INFORMATION FOR SEQ ID NO:17:

(i) SEQUENCE CHARACTERISTICS:
    (A) LENGTH: 25 amino acids
    (B) TYPE: amino acid
    (C) STRANDEDNESS: single
    (D) TOPOLOGY: linear ( i i ) MOLECULE TYPE: protein ( x i ) SEQUENCE DESCRIPTION: SEQ ID NO:17:

Val Glu Thr Lys Ala Ala Ala Ile Glu Ala Ile Gly Ala Ala Leu His
1               5                   10                  15

Leu Pro Ser Pro Glu Ala Ala Gln Ala
            20              25

( 2 ) INFORMATION FOR SEQ ID NO:18:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:18:

Glu Ala Ala Gln Ala Ala Leu Glu Ala Leu Glu Glu Ala Ala Val Ser
1               5                   10                  15

Leu Leu Pro His Val Pro Val Ile Met
            20              25

( 2 ) INFORMATION FOR SEQ ID NO:19:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:19:

Val Pro Val Ile Met Gly Asp Asp Cys Ser Cys Arg Asp Glu Ala Phe
1               5                   10                  15

Gln Gly His Phe Ile Pro Glu Pro Asn
            20              25

( 2 ) INFORMATION FOR SEQ ID NO:20:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:20:

Ile Pro Glu Pro Asn Val Thr Glu Val Pro Ile Glu Pro Thr Val Gly
1               5                   10                  15

Asp Val Glu Ala Leu Lys Leu Arg Ala
            20              25

( 2 ) INFORMATION FOR SEQ ID NO:21:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:21:

```
Leu Lys Leu Arg Ala Ala Asp Leu Thr Ala Arg Leu Gln Asp Leu Glu
1               5                   10                  15

Ala Met Ala Leu Ala Arg Ala Glu Ser
            20                  25
```

( 2 ) INFORMATION FOR SEQ ID NO:22:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:22:

```
Glu Ala Met Ala Leu Ala Arg Ala Glu Ser Ile Glu Asp Ala Arg Ala
1               5                   10                  15

Ala Ser Met Pro Ser Leu Thr Glu Val
            20                  25
```

( 2 ) INFORMATION FOR SEQ ID NO:23:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:23:

```
Met Pro Val Ile Ser Thr Gln Thr Ser Pro Val Pro Ala Pro Arg Thr
1               5                   10                  15

Arg Lys Asn Lys Gln Thr Gln Ala Ser Tyr Pro Val Ser Ile Lys Thr
                20                  25                  30

Ser Val Glu
        35
```

( 2 ) INFORMATION FOR SEQ ID NO:24:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:24:

```
Pro Val Ser Ile Lys Thr Ser Val Glu Arg Gly Gln Arg Ala Lys Arg
1               5                   10                  15

Lys Val Gln Arg Asp Ala Arg Pro Arg Asn Tyr Lys Ile Ala Gly Ile
                20                  25                  30

His Asp
```

( 2 ) INFORMATION FOR SEQ ID NO:25:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:25:

-continued

```
Ala His Gly Trp Gly Arg Gln Asp Pro Arg His Lys Ser Arg Asn Leu
1               5                   10                  15
Gly Ile Leu Leu Asp Tyr Pro Leu Gly Trp Ile Gly Asp Val Thr
                20                  25              30
```